(12) United States Patent
Delp et al.

(10) Patent No.: US 12,142,364 B2
(45) Date of Patent: Nov. 12, 2024

(54) SYSTEMS AND METHODS THAT PROVIDE A POSITIVE EXPERIENCE DURING WEIGHT MANAGEMENT

(71) Applicants: Stella K. Delp, Stanford, CA (US); Scott Lee Delp, Stanford, CA (US)

(72) Inventors: Stella K. Delp, Stanford, CA (US); Scott Lee Delp, Stanford, CA (US)

( * ) Notice: Subject to any disclaimer, the term of this patent is extended or adjusted under 35 U.S.C. 154(b) by 0 days.

(21) Appl. No.: 16/971,822

(22) PCT Filed: Feb. 27, 2019

(86) PCT No.: PCT/US2019/019894
§ 371 (c)(1),
(2) Date: Aug. 21, 2020

(87) PCT Pub. No.: WO2019/169034
PCT Pub. Date: Sep. 6, 2019

(65) Prior Publication Data
US 2020/0395116 A1    Dec. 17, 2020

Related U.S. Application Data

(60) Provisional application No. 62/636,014, filed on Feb. 27, 2018.

(51) Int. Cl.
*G16H 20/70* (2018.01)
*G01G 19/414* (2006.01)
(Continued)

(52) U.S. Cl.
CPC .......... *G16H 20/70* (2018.01); *G01G 19/414* (2013.01); *G01G 19/44* (2013.01); *G06T 19/006* (2013.01);
(Continued)

(58) Field of Classification Search
CPC ...... G01G 19/44; G01G 19/414; G01G 23/18; G01G 23/36; G01G 23/365;
(Continued)

(56) References Cited

U.S. PATENT DOCUMENTS

| 3,750,158 A | 7/1973 | Anastassakis |
| 4,318,447 A | 3/1982 | Northcutt |

(Continued)

FOREIGN PATENT DOCUMENTS

| CN | 104568101 A | 4/2015 |
| CN | 206756298 U | 12/2017 |

(Continued)

OTHER PUBLICATIONS

Tylka et al., "The Weight-Inclusive versus Weight-Normative Approach to Health: Evaluating the Evidence for Prioritizing Well-Being over Weight Loss", Jul. 2014, Hindawi Publishing Corporation, Journal of Obesity, vol. 2014, Article ID 983495, p. 1-18 (Year: 2014).*

(Continued)

*Primary Examiner* — Jonathan Ng
*Assistant Examiner* — Hunter J Rasnic
(74) *Attorney, Agent, or Firm* — Shay Glenn LLP

(57) ABSTRACT

A device for weight management includes a platform, a weight sensor configured to measure a weight of a user when the user is positioned on the platform, an input mechanism configured to receive input related to target weight of the user, a converter configured to convert the measured weight to a non-numerical output based upon the input, and a display configured to provide the non-numerical output to the user without providing the measured weight to the user.

7 Claims, 16 Drawing Sheets

(51) Int. Cl.
*G01G 19/44* (2006.01)
*G06T 19/00* (2011.01)
*G16H 10/60* (2018.01)
*G16H 20/60* (2018.01)
*G16H 50/30* (2018.01)

(52) U.S. Cl.
CPC ............ *G16H 10/60* (2018.01); *G16H 20/60* (2018.01); *G16H 50/30* (2018.01)

(58) Field of Classification Search
CPC ........... G01G 23/3735; G01G 23/3728; G01G 19/50; G01G 21/22; G01G 17/08; G01G 19/4146; G01G 13/24; G01G 21/283; G01G 23/42; G01G 19/4144; G01G 11/04; G01G 19/005; G01G 19/035; G01G 19/14; G01G 19/18; G01G 19/415; G01G 19/56; G01G 7/02; G01G 7/06; G01G 19/024; G01G 19/60; G06F 16/245; G06F 3/04812; G06F 3/04817; G09B 19/0092; G16H 10/60; G16H 20/60; G16H 20/70; G16H 40/60; G16H 40/67; G06T 19/006
See application file for complete search history.

(56) References Cited

U.S. PATENT DOCUMENTS

| | | | |
|---|---|---|---|
| 4,423,792 A | 1/1984 | Cowan | |
| 4,576,244 A | 3/1986 | Zeigner et al. | |
| 4,629,015 A | 12/1986 | Fried et al. | |
| 4,951,197 A * | 8/1990 | Mellinger | G16H 20/60 600/300 |
| 6,080,106 A * | 6/2000 | Lloyd | G16H 40/67 600/300 |
| D460,010 S | 7/2002 | Robinson | |
| 6,541,714 B2 | 4/2003 | Montagnino | |
| 6,617,530 B1 | 9/2003 | Lin | |
| 6,679,854 B2 | 1/2004 | Honda et al. | |
| 6,816,807 B2 | 11/2004 | Kriger | |
| 6,975,961 B1 | 12/2005 | Hong | |
| 7,170,016 B2 | 1/2007 | Dumornay et al. | |
| 7,265,301 B2 * | 9/2007 | Simberg | G01G 19/44 128/921 |
| 7,304,252 B1 | 12/2007 | Hunt et al. | |
| 7,572,987 B2 | 8/2009 | Fenn | |
| 7,705,249 B2 | 4/2010 | Rindermann et al. | |
| 7,924,278 B2 * | 4/2011 | Loop | G06T 15/40 345/423 |
| 7,932,472 B2 | 4/2011 | Oseko | |
| 7,994,439 B2 * | 8/2011 | Daniels | G01G 19/4146 177/25.13 |
| 8,362,903 B2 * | 1/2013 | Lindh | G01G 19/44 340/573.1 |
| 8,475,367 B1 * | 7/2013 | Yuen | G16H 50/30 177/4 |
| 8,536,469 B2 | 9/2013 | Sato et al. | |
| 8,541,700 B2 * | 9/2013 | Sato | G01G 19/4146 177/25.19 |
| 8,690,578 B1 * | 4/2014 | Nusbaum | G16Z 99/00 705/2 |
| 8,892,481 B2 | 11/2014 | Landers | |
| 9,157,787 B2 * | 10/2015 | Sharma | G01G 19/44 |
| 9,652,992 B2 * | 5/2017 | Kaleal, III | G06T 19/00 |
| 9,766,117 B2 | 9/2017 | Gomez | |
| 9,891,095 B2 * | 2/2018 | Villard | G01G 23/3728 |
| 10,004,407 B2 * | 6/2018 | Kovacs | A61B 5/0205 |
| 2004/0225533 A1 * | 11/2004 | Cosentino | G16H 40/63 600/300 |
| 2005/0247494 A1 | 11/2005 | Montagnino | |
| 2006/0122470 A1 * | 6/2006 | Schulz | G01G 19/50 600/300 |
| 2006/0241970 A1 | 10/2006 | Winiarski | |
| 2008/0294370 A1 | 11/2008 | Kriger | |
| 2009/0044987 A1 * | 2/2009 | Taylor | G01G 23/3735 177/245 |
| 2009/0178858 A1 * | 7/2009 | Daniels | G01G 19/4146 177/25.19 |
| 2010/0049471 A1 * | 2/2010 | Gage | G16H 20/60 702/173 |
| 2010/0228521 A1 | 9/2010 | Hamamoto | |
| 2012/0330683 A1 | 12/2012 | Ledwidge et al. | |
| 2013/0043997 A1 * | 2/2013 | Cosentino | G16H 10/20 340/573.1 |
| 2013/0233627 A1 | 9/2013 | Vidal et al. | |
| 2013/0333955 A1 * | 12/2013 | Jefferson | G01G 23/18 177/1 |
| 2014/0214446 A1 * | 7/2014 | Nusbaum | A63B 24/0062 705/2 |
| 2014/0257741 A1 * | 9/2014 | Chupp | G01G 23/3728 702/173 |
| 2014/0289312 A1 * | 9/2014 | Jafarifesharaki | H04L 63/08 709/203 |
| 2015/0107910 A1 * | 4/2015 | Villard | G16H 20/60 177/25.12 |
| 2015/0339946 A1 * | 11/2015 | Pacione | G09B 19/00 434/236 |
| 2016/0086500 A1 * | 3/2016 | Kaleal, III | A61B 5/45 434/257 |
| 2016/0213334 A1 | 7/2016 | Oleson | |
| 2017/0082483 A1 * | 3/2017 | Vogel | G01G 21/28 |
| 2017/0098040 A1 * | 4/2017 | Wolin | G16Z 99/00 |
| 2017/0146391 A1 | 5/2017 | Kovacs et al. | |
| 2017/0365182 A1 * | 12/2017 | Lavi | G09B 19/0092 |
| 2017/0372017 A1 * | 12/2017 | Steffen | G16H 40/67 |
| 2018/0000347 A1 * | 1/2018 | Perez | A61N 1/36014 |
| 2018/0045558 A1 * | 2/2018 | Moore | G01G 19/50 |
| 2018/0294053 A1 | 10/2018 | Runyon et al. | |
| 2019/0033122 A1 | 1/2019 | Lin | |

FOREIGN PATENT DOCUMENTS

| | | |
|---|---|---|
| CN | 109238426 A | 1/2019 |
| DE | 202010017987 U1 | 9/2013 |
| EP | 1076230 B1 | 11/2004 |
| EP | 2183553 B1 | 1/2013 |
| KR | 2010004886 U | 5/2010 |
| KR | 20160049289 A | 5/2016 |
| KR | 20170033958 A | 3/2017 |
| WO | WO2004/021314 A2 | 3/2004 |
| WO | WO2007/102733 A1 | 9/2007 |
| WO | WO2009/033328 A1 | 3/2009 |
| WO | WO2014/113005 A2 | 7/2014 |

OTHER PUBLICATIONS

Shapa; The revolutionary scale and personalized wellness app; (Product Discription); 11 pages; retrieved from the internet (https://www.myshapa.com/) on Dec. 2020.

\* cited by examiner

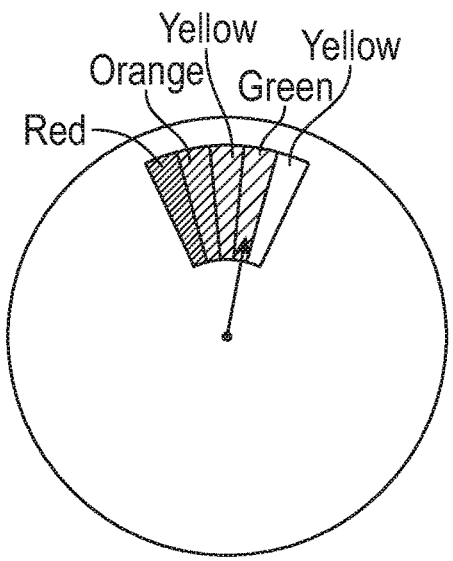
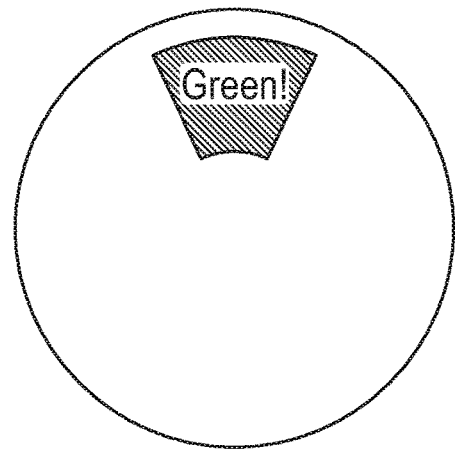
FIG. 11A  FIG. 11B
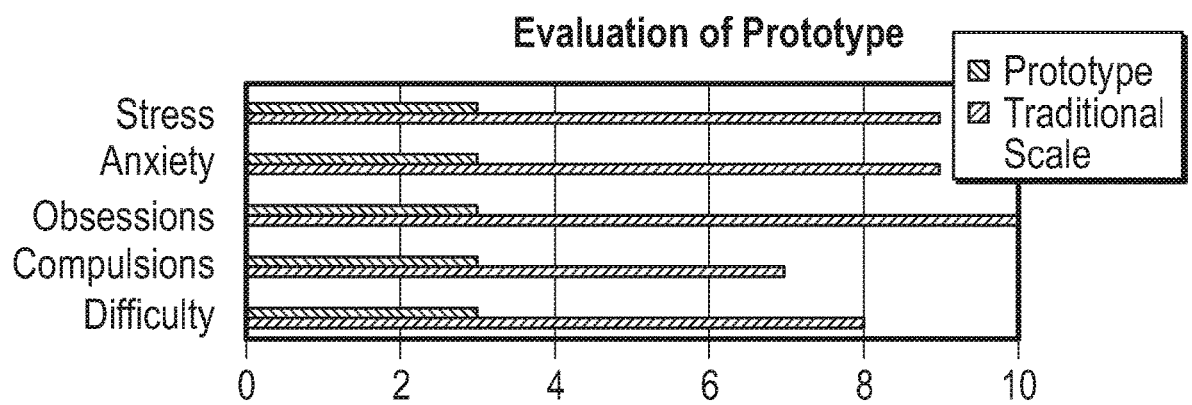
FIG. 12

SYSTEMS AND METHODS THAT PROVIDE A POSITIVE EXPERIENCE DURING WEIGHT MANAGEMENT

CROSS REFERENCE TO RELATED APPLICATIONS

This application is a U.S. National Phase Application Under 35 U.S.C. § 371 of International Application No. PCT/US2019/019894, filed on Feb. 27, 2019, titled "SYSTEMS AND METHODS THAT PROVIDE A POSITIVE EXPERIENCE DURING WEIGHT MANAGEMENT," now International Publication No. WO 2019/169034, which claims priority to U.S. Provisional Patent Application No. 62/636,014 titled "SYSTEMS AND METHODS THAT PROVIDE A POSITIVE EXPERIENCE DURING WEIGHT MANAGEMENT," filed on Feb. 27, 2018, the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Millions of individuals need to adjust or maintain their weight to manage their health. The universal method for managing weight is to stand on a scale and observe a number that represents the person's weight. A wide variety of scales have been developed that measure and report the numerical value of a person's weight or a numerical value indicating weight change. Unfortunately, pinning one's health and self esteem to a number has devastating psychological effects for many people. Individuals can feel judged by the number and alone in the process of weight management.

The negative health consequences of current standards for weight management are staggering. Obesity, due in part to poor weight management, affects over one third of the world's population and is associated with increased risk of nearly every chronic condition, from diabetes to mental illness. It increases the risk of stroke and cardiovascular disease, certain cancers, and osteoarthritis. In the year 2000, 15% of deaths in the U.S. were attributable to excess weight. Further, eating disorders affect over 30 million people of all ages and genders in the United States. Such eating disorders have the highest mortality rate of any mental illness; every 62 minutes, one person dies as a direct result from an eating disorder.

Obsession with weight is a common and devastating feature for many individuals who struggle with eating disorders and/or obesity. Current weight management tools, including traditional scales and apps, can trigger and heighten such obsession, including for those with obsessive compulsive disorders (OCD). Indeed, some individuals with OCD have reported that up to 70 percent of their thoughts during the day are concerning weight. These individuals tend to plan a majority of their life around weight, making it nearly impossible to lead a healthy balanced life. With an estimated 45 million Americans dieting each year, and an estimated 3.3 million people in the U.S. struggling with OCD, there is significant overlap in these groups. Further, such obsession with numerical weight values contributes to major health problems, including anorexia nervosa, obsessive compulsive disorder, depression, and other conditions.

Thus, there is a critical need for improved means to measure, report and track body weight that does not carry the negative psychological valance and negative health consequences of the current methods and devices. A device is needed to better manage weight to keep people healthy and to help manage obesity, diabetes, anorexia nervosa, bulimia nervosa, and other conditions. Despite this long-standing need, there are no scales for successfully achieving the goal of positive psychological valance during weight management.

SUMMARY OF THE DISCLOSURE

In general, in one embodiment, a device for weight management includes a platform, a weight sensor configured to measure a weight of a user when the user is positioned on the platform, an input mechanism configured to receive input related to target weight of the user, a converter configured to convert the measured weight to a non-numerical output based upon the input, and a display configured to provide the non-numerical output to the user without providing the measured weight to the user. The display is further configured to provide supportive feedback to the user that is unrelated to the measured weight.

This and any other embodiments can include one or more of the following. The device can include a colored graph that is configured to be retrofitted over an analog scale. The display can include first, second, and third zones. The first zone can correspond to a measured weight within a target weight range, the second zone can correspond to a measured weight that is outside of the target weight range by a first percentage, and the third zone can correspond to a measured weight that is outside of the target weight range by a second percentage that is greater than the first percentage. The first percentage can be greater than 0% and less than 3%-10%. The zones can be colored zones. The converter can be a controller that is part of the platform. The converter can be part of an app. The display can be on the platform. The display can be part of an app. The display can be configured to provide audio or visual feedback. The platform can be configured to be customized with context from the user. The context can include photos, words, sounds, or images. The device can be configured to provide the measured weight to a healthcare provider. The device can further include a communication element configured to allow the user to receive feedback from a support member. The display can be configured to provide blended colored zones that provide the non-numerical output to the user. The non-numerical output can be based on a health tensor. The converter can be configured to smooth the weight measurement. The non-numerical output can provided at least one minute after the weight measurement is taken. The non-numerical output can be provided on the display fewer times than the weight measurement is taken. The non-numerical output can be customized by the user. The device can further include an alert mechanism configured to activate if a goal weight of the input corresponds to an unhealthy body mass index. The device can be configured to automatically alert a support team when the user steps on the platform. The supportive feedback can be configured to create a positive mindset in the user.

In general, in one embodiment, a method of weight management includes: (1) obtaining input data related to a target weight of a user; (2) measuring a weight of the user; (3) converting the measured weight to a non-numerical output based upon the input data; (4) providing the non-numerical output to the user without providing the measured weight to the user; and (5) providing supportive feedback to the user that is unrelated to the measured weight so as to promote a positive mindset for the user.

This and any other embodiments can include one or more of the following. Providing the non-numerical output to the user can include indicating a zone within which the measured weight falls. There can be first, second, and third zones. The first zone can correspond to a measured weight that is within a target weight range, the second zone can correspond to a measured weight that is outside of the target weight range by a first percentage, and the third zone can correspond to a measured weight that is outside of the target weight range by a second percentage that is greater than the first percentage. The first percentage can be greater than 0% and less than 3%-10%. The zones can be colored zones. Providing the non-numerical output to the user can include providing the output on an app. Measuring a weight of the user can include measuring the weight with a weight sensor while the user is positioned on a platform. Providing the non-numerical output to the user can include providing the output on a display on the platform. The non-numerical output can include audio or visual feedback. The method can further include obtaining customized input from the user comprising photos, words, sounds, or images. The method can further include providing the measured weight to a healthcare provider. Providing the non-numerical output to the user can include providing the non-numerical output at least one minute after measuring the weight. The method can further include limiting a number of times that the non-numerical output is provided to the user. The method can further include alerting the user if a goal weight of the input corresponds to an unhealthy body mass index. The method can further include alerting a support team member when the weight measurement is taken. The method can further include measuring the user's response to the non-numerical output and adapting future output based upon the response. The method can further include adjusting a goal weight or weight ranges over time. The method can be used to treat congestive heart failure, anorexia nervosa, athletes, eating disorders, obesity, obsessive-compulsive disorder, anxiety, depression, cardio vascular disease, hypertension, stroke, gallbladder disease, diabetes, bone or joint disease, sleep apnea, osteoarthritis, gout, fatty liver disease, kidney disease, complications in pregnancy, or cancer.

In general, in one embodiment, a method of managing weight for patients with anorexia nervosa includes: (1) measuring a patient's weight with a weight sensor of a weight management system; (2) providing an indication from the weight sensor that a weight measurement has been taken; and (3) sending the weight measurement to medical personnel without providing the weight measurement to the patient.

In general, in one embodiment, a device for weight management of athletes or patients with anorexia nervosa or congestive heart failure can include a platform, a weight sensor, and a controller that is configured to perform any of the methods described herein.

In general, in one embodiment, a method of managing weight for patients with anorexia nervosa includes: (1) measuring a patient's weight with a weight sensor; (2) providing an indication from the weight sensor that weight measurement has been taken; (3) comparing the measured weight with a previous measured weight to obtain a differential weight, and (4) providing positive feedback to the user based upon the comparison without providing the measured weight or the differential weight to the patient.

This and any other embodiments can include one or more of the following. The method can further include receiving input regarding the patient's desired weight range or time based weight goals. The method can further include determining a weight change threshold or zones for the patient's weight. The method can further include receiving input regarding customization of the weight management system. Measuring the patient's weight can include measuring the weight as the patient stands on a platform of the weight management system.

In general, in one embodiment, a method of managing weight for patients with anorexia nervosa includes: (1) obtaining information regarding a patient's threshold weight range; (2) measuring the patient's weight with a weight sensor; (3) if the patient's weight is within the threshold range, displaying a first non-numerical output; (4) if the patient's weight is below the threshold weight range, displaying a second non-numerical output and providing feedback comprising one or more of that the patient should increase nutritional intake, decrease physical activity, or contact medical personnel.

This and any other embodiments can include one or more of the following. The method can further include receiving input regarding customization of the weight management system. Measuring the patient's weight can include measuring the weight as the patient stands on a platform of the weight management system. Providing the non-numerical output to the user can include providing the non-numerical output at least one minute after measuring the weight. The method can further include limiting a number of times that the non-numerical output is provided to the user. Providing the non-numerical output to the user can include indicating a zone within which the measured weight falls. There can be first, second, and third zones. The first zone can correspond to a measured weight that is within a target weight range, the second zone can correspond to a measured weight that is outside of the target weight range by a first percentage, and the third zone can correspond to a measured weight that is outside of the target weight range by a second percentage that is greater than the first percentage. The first percentage can be greater than 0% and less than 3%-10%.

In general, in one embodiment, a device for weight management includes a platform, a weight sensor configured to measure a weight of the patient when a patient is positioned on the platform, and a controller, wherein the controller is configured to have first, second, and third settings. In the first setting, the controller is configured to obtain a weight measurement from a patient positioned on the platform and to send the weight measurement to a healthcare provider without providing the weight measurement to the patient. In the second setting, the controller is configured to obtain a weight measurement from a patient positioned on the platform and to provide non-numerical feedback to the patient that relates the obtained weight measurement with previous weight measurements. In the third setting, the controller is configured to obtain a weight measurement from a patient positioned on the platform and to provide non-numerical feedback to the patient that relates the obtained weight measurement with a target weight range.

In general, in one embodiment, a method of managing weight for patients with congestive heart failure includes: (1) obtaining information regarding a patient's starting weight and weight change threshold; (2) measuring the patient's weight with a weight sensor; (3) providing an indication from the weight sensor that a weight measurement has been taken without providing the weight measurement to the patient; and (4) if the measured weight is more than the weight change threshold, indicating that the patient should contact medical personnel.

This and any other embodiments can include one or more of the following. The weight change threshold can include a weight gain of 3 pounds or less in 24 hours. The weight change threshold can include a daily weight change threshold and a weekly weight change threshold. The method can further include proving positive non-numerical feedback to the patient if the measured weight is less then the weight change threshold.

In general, in one embodiment, a method of managing weight for athletes includes: (1) obtaining information regarding an athletes starting weight and goal weight; (2) measuring the athletes weight with a weight sensor; (3) providing non-numerical feedback to the athlete that indicates whether the athlete is on track to meet the goal weight without providing the measured weight to the athlete; and (4) providing the measured weight to a coach or medical personnel.

Any of the device embodiment s can be configured to provide the measured weight or weight measurement to the user intermittently. Similarly, any of the method embodiments can include providing the measured weight or weight measurement to the user intermittently (i.e., less frequently than the non-numerical feedback is provided).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 11A shows an exemplary display including five different colored zones that provide non-numerical weight information to the user.

FIG. 11B shows an exemplary display that change color based upon the weight of the user.

FIG. 12 shows the results of the evaluation of a prototype weight management system.

DETAILED DESCRIPTION

Described herein are systems and methods that provide a positive psychological experience for individuals in support of their weight management goals. In particular, described herein are health feedback or weight management systems and methods that can display an individual's weight relative to a weight target, weight threshold, weight range, approximate weight, approximate weight threshold, or approximate weight range, without the use of numbers. Weight or weight correlation can instead be displayed via colors, sounds, or other means. In some embodiments, the weight management systems establish a health tensor that is computed based on measures of physical and mental well-being, including weight, weight change, and anxiety, and other variables, which can be computed and conveyed in non-numerical terms. The weight management systems can be customized with inspirational words, pictures, music, voices, videos, and/or a social network to enable the user to have a positive relationship with his or her weight measurement and the process of managing weight and health.

The weight management systems described herein advantageously harness the power of mindset to promote positive change by, for example, delivering information that alters metabolism and creates a healthy mindset rather than creating a mindset of inadequacy and illness. The weight management systems can include other features that make the process of managing weight a positive experience, including: (1) personalization of desired weight ranges and tolerances for these ranges; (2) goals that vary over time to encourage goal attainment; (3) graphical narratives for tracking and motivating users progress over time; (4) qualitative and quantitative information transmitted to a plurality of users of the device; and/or (5) social support that enables users to connect with others to reduce fear and encourage goal attainment.

In some embodiments, a weight management system can include software and/or hardware kits to retrofit current scales. In some embodiments, a weight management system can include an artificial intelligence system with behavioral modeling to ensure safe use of the weight management system and to optimize goal attainment for each individual.

In some embodiments, the weight management system can include a mechanism to record an emotional response to its use so as to optimize its feedback and promote a positive experience and goal attainment. The weight management systems described herein can advantageously change the valence of the experience of weight management from negative to positive.

Figure 1A:
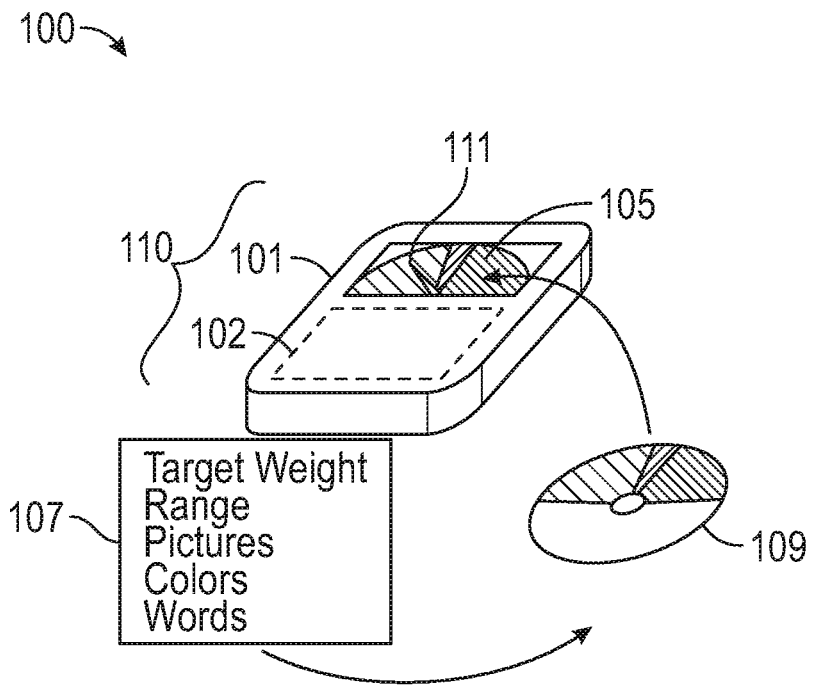
FIG. 1A shows an exemplary weight management system that can be retrofit to an existing analog scale.

Referring to FIG. 1A, a weight management system 100 can include a unit 110 comprising a platform 101 having a weight sensor 102 therein. A non-numerical display 105 of the unit 110 can be positioned on the platform 101. The system 100 can accept user input 107, for example of a target weight range or healthy weight zones. The input 107 can be provided, for example, prior to manufacturing of the unit 110. A converter 109 of system 100 can correlate the user input 107 with a non-numeric feedback mechanism. For example, a range of colors can be used to indicate underweight, healthy, or overweight. That converter 109 can be used as part of the display 105 (in conjunction with an indicator 111). For example, the converter 109 can be provided to the user to replace or be placed over the numerical scale of a standard weight scale (i.e., the platform 101 and sensor 102 can be part of a standard scale). The indicator 111 (either part of the standard weight scale or provided with the converter 109) can provide the user with non-numerical feedback based on the reading from the sensor 102. In some embodiments, the system 100 can be a purely mechanical or analog system.

Figure 1B:
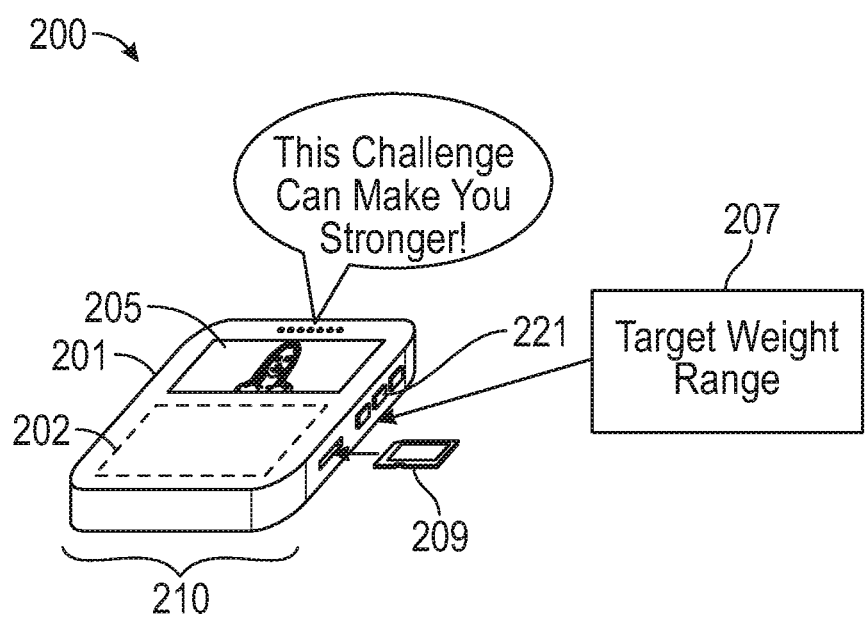
FIG. 1B shows another exemplary weight management system that is digital and wholly contained in a single unit.

Referring to FIG. 1B, a weight management system 200 includes a standalone unit 210. The unit 210 includes a platform 201 having a weight sensor 202 therein. A non-numerical display 205 can be positioned on the platform 201. The system 200 can accept user input 207 (for example, through a control or set of buttons 221). Additionally, the system 200 can include a converter 209 that converts the user input 207 to a nonnumeric feedback system. For example, the converter 209 can include a memory and a central processing unit with an algorithm to convert the measured weight to non-numerical feedback. The display 205 can include, for example, visual feedback and/or can include audio feedback.

Figure 1C:
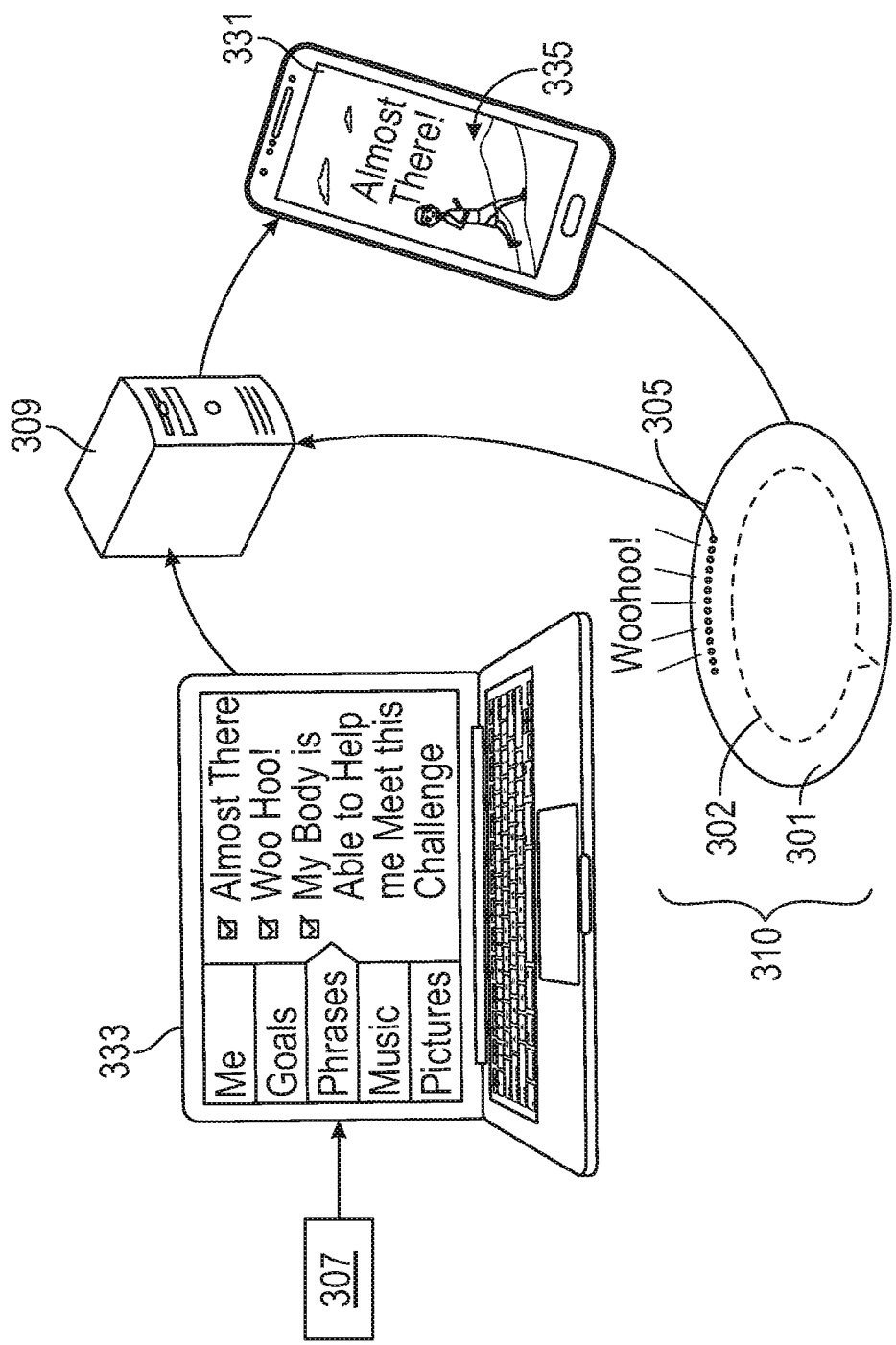
FIG. 1C shows another exemplary weight management system that includes a networked controller and app.

Referring to FIG. 1C, a weight management system 300 includes a unit 310. The unit 310 includes a platform 301 having a weight sensor 302 therein. The unit 310 further includes a display 305 that provides only audio feedback and not visual feedback (though in other embodiments, visual feedback may be included as well). The unit 310 can communicate with a converter 309 (which can be a central processing unit, memory, and communication channel within the unit 310 or can be a controller or server to store data and convert feedback from the sensor 301 to appropriate feedback). The converter 309 can in turn be connected, for example, to an app 331 that can provide non-numerical feedback. User input 307 can be provided, for example, through a standard computer 333 and/or through the app 331 to the converter 309. The app 331 may show progress via a visual narrative 335 that advances based on a user's engagement and goal attainment.

Figure 2A:
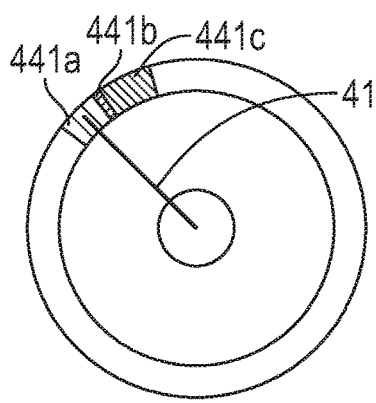
FIGS. 2A-2C show an exemplary display with three zones to provide a non-numerical indication of measured weight relative to goal weight.
Figure 2B:
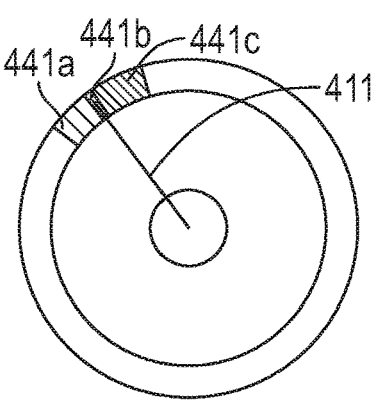
Figure 2C:
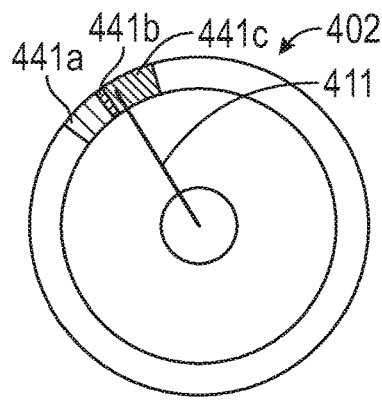

The weight management systems 100, 200, and 300 can be used to enable weight management while facilitating self-acceptance and health. The weight management systems 100, 200, and 300 do not display to an individual the individual's weight in a numeric value or weight converted to an alternative numerical value. Instead, alternate non-numerical feedback is provided. Referring to FIGS. 2A-2C, in one embodiment, the display 402 can include three zones 441a, 441b, and 441c. In one embodiment, zone 441a can indicate significantly underweight (e.g., more than 3% of body weight away from the goal weight range), zone 441b can indicate slightly underweight (e.g. up to 3% of body weight away from the goal weight range), and zone 441c can indicate that the measured weight is within the goal weight range. The zones 441a-c can be different colors. For example, the zones 441a-c can be red, yellow, and green. An indicator 411 can move based on reading from the weight center to indicate which zone 441a-c the user falls within at a particular measurement. The zones 441a-c can thus be tailored to the individual. Additionally, in some embodiments, the zones 441a-c can be updated and/or change over time.

Figure 4:
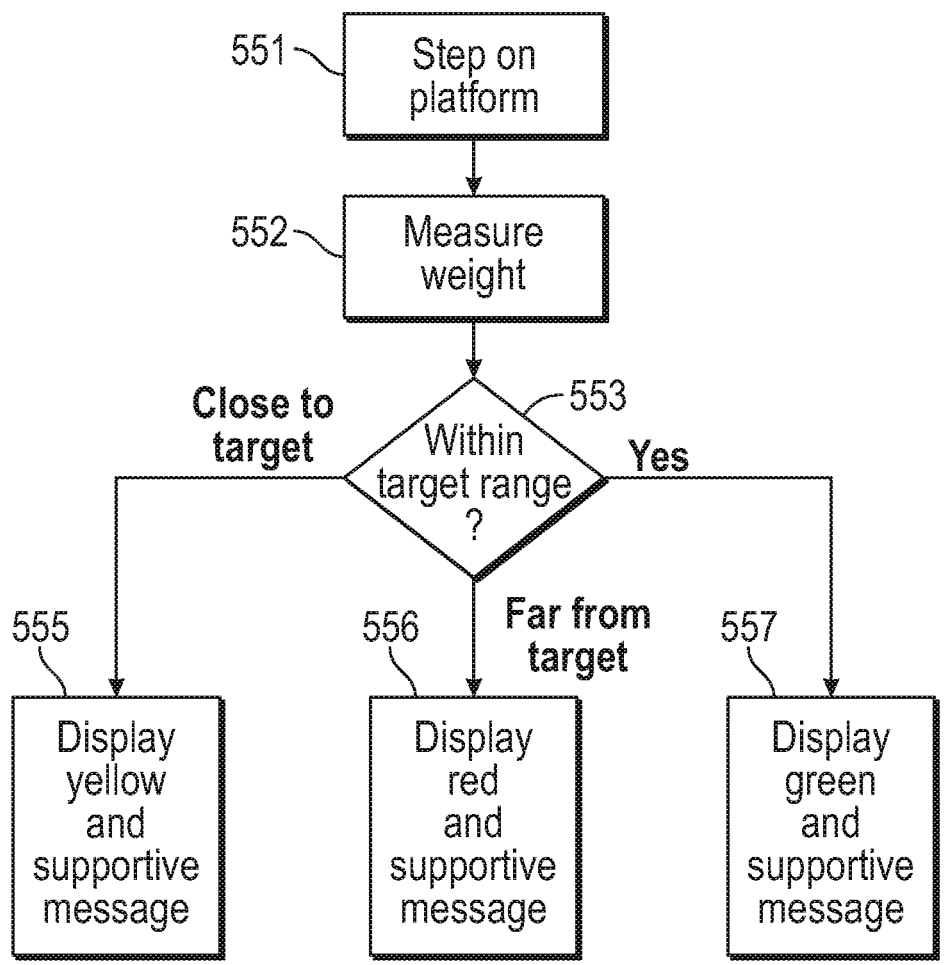
FIG. 4 is a flow chart showing an exemplary method of use of a weight management system.

An exemplary method of using a weight management system e.g., of system 100, 200, or 300) that includes the display 402 is shown in FIG. 4. At step 551, the user can step on the platform that includes a weight sensor. At step 552, the user's weight can be measured with the weight sensor. At step 553, the sensed weight can be provided in non-numerical form relative to the target weight. For example, at step 555, if close to target weight, then the indicator can display yellow and a supportive message. At step 556, if far from the target weight, then the display can indicate red and a supportive message. At step 557, if within target range, then the display can indicate green and provide a supportive message.

Figure 3A:
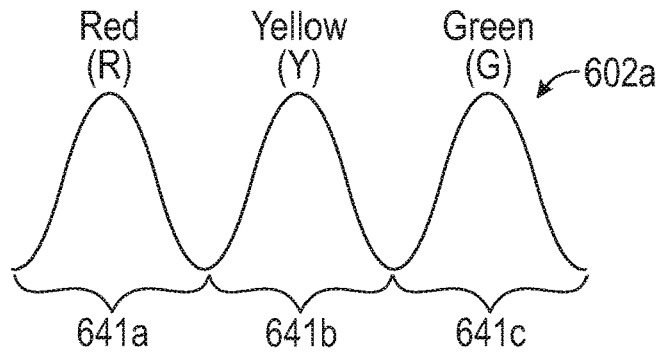
FIG. 3A shows a display with three separated color zones.
Figure 3B:
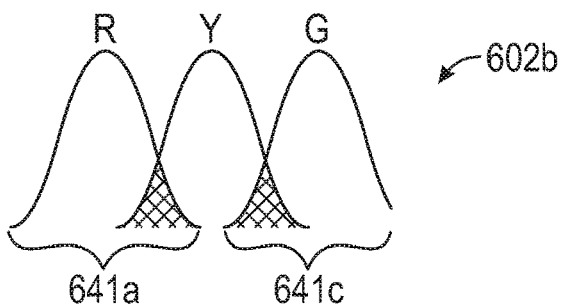
FIG. 3B shows a display with partially overlapping color zones.
Figure 3C:
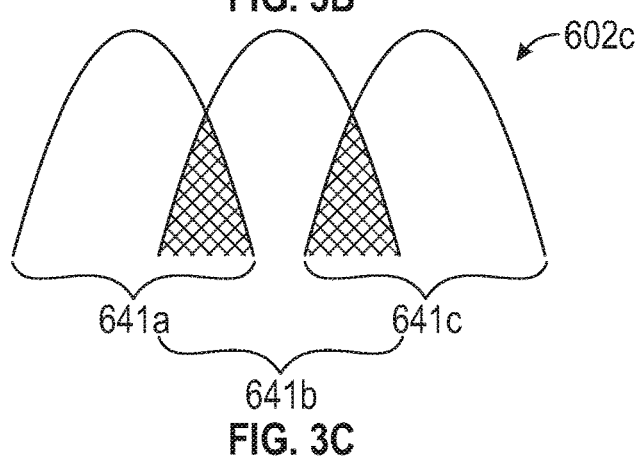
FIG. 3C shows a display with further overlapping color zones.

In some embodiments, three different colors are used to indicate three different zones of weight. In other embodiments, three or more colors can be used. In some embodiments, the display can show blended zones of color. For example, FIG. 3A a shows a display 602a with separate zones 641a-c. FIG. 3B shows a display 602b with partially blended zones 641a-c while FIG. 3C shows significantly overlapping zones 641a-c. The overlapping zones can, in some embodiments, encourage flexibility of thinking (i.e., can reduce obsessions and rigid thinking). The overlapping portions can, for example, be presented in a color that is a blended version of the two overlapping colors, thus providing feedback along a color spectrum that includes many colors.

In some embodiments, the feedback to the users can be based on a health tensor, which is a mathematical object represented by an array of components that are functions of the coordinates of a health space. Here, the word space is used in sense of a branch of mathematics called linear algebra and is well known to individuals who are skilled in the art. Components of the heath space include measures of physical and mental well-being, such as weight, weight change, target weight, anxiety, compulsive behavior status, disease status, and stage of recovery. Once a health tensor is formed, mathematical operations from linear algebra, such as principal components analysis, can be used to transform the health tensor. Computations based on the health tensor can be used to determine the type of feedback to be conveyed to the user.

Figure 9A:
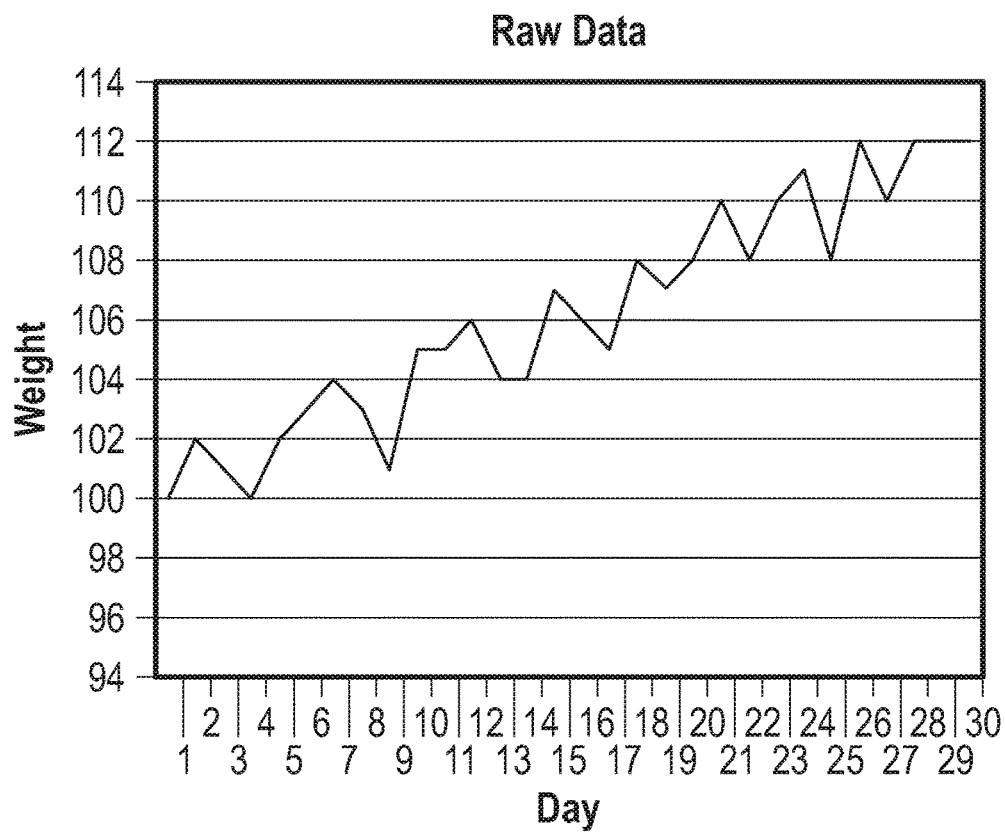
FIG. 9A is a graph showing exemplary raw data of weight gain over time.
Figure 9B:
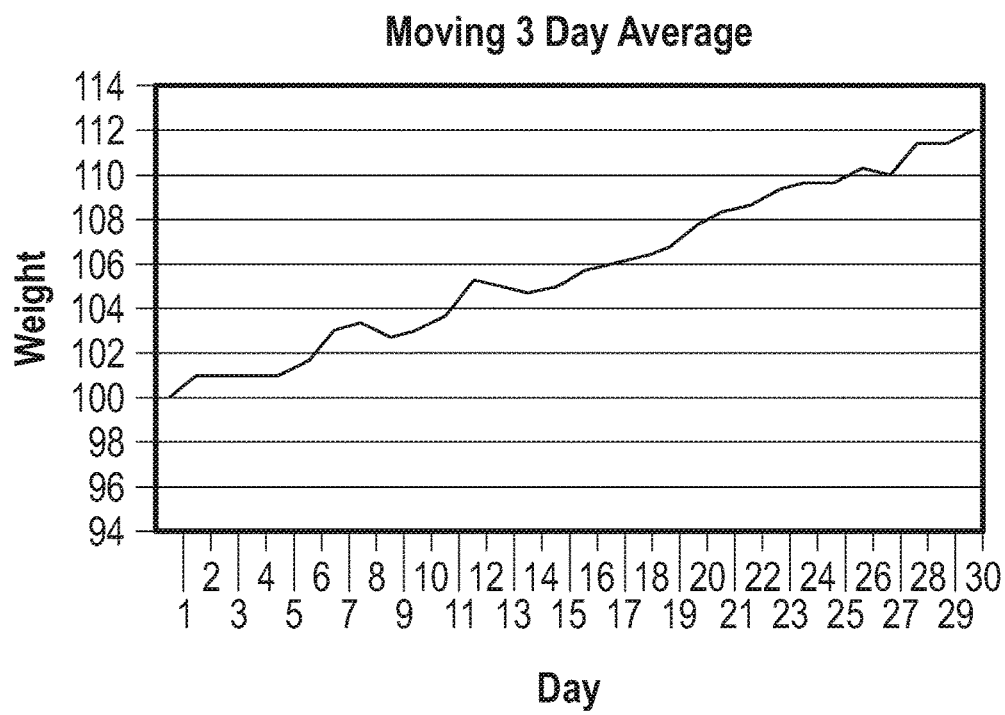
FIG. 9B is a graph showing the data of FIG. 9A smoothed as a moving 3-day average.
Figure 10A:
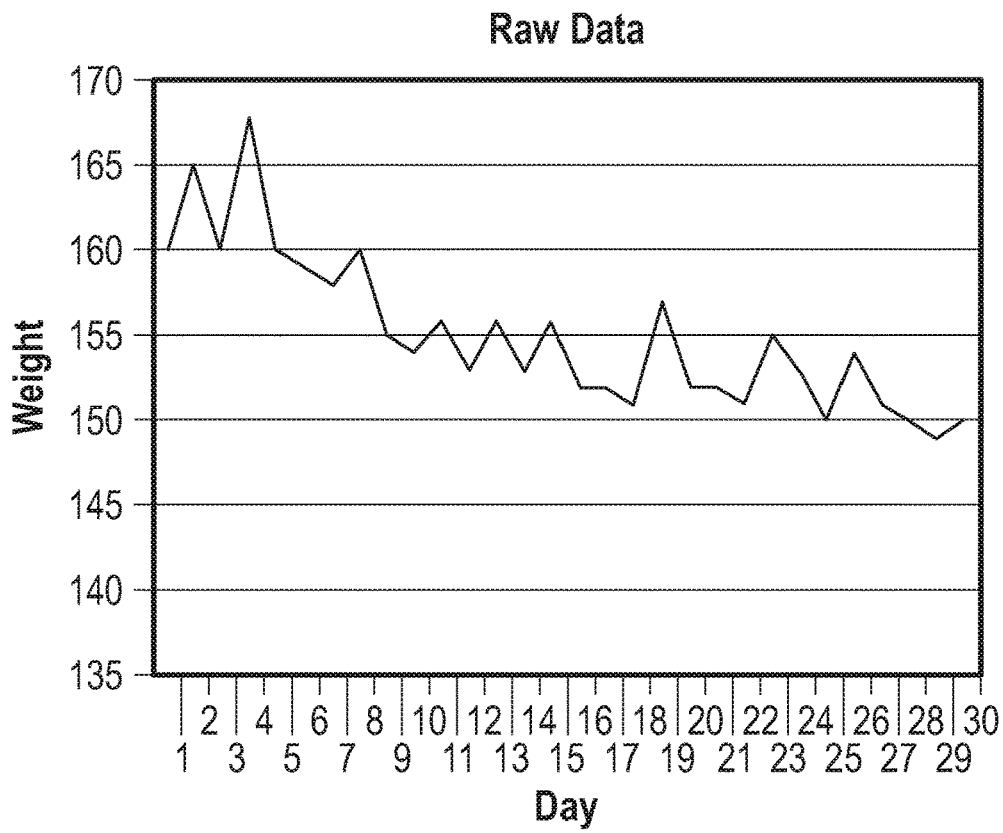
FIG. 10A is a graph showing exemplary raw data of weight loss over time.
Figure 10B:
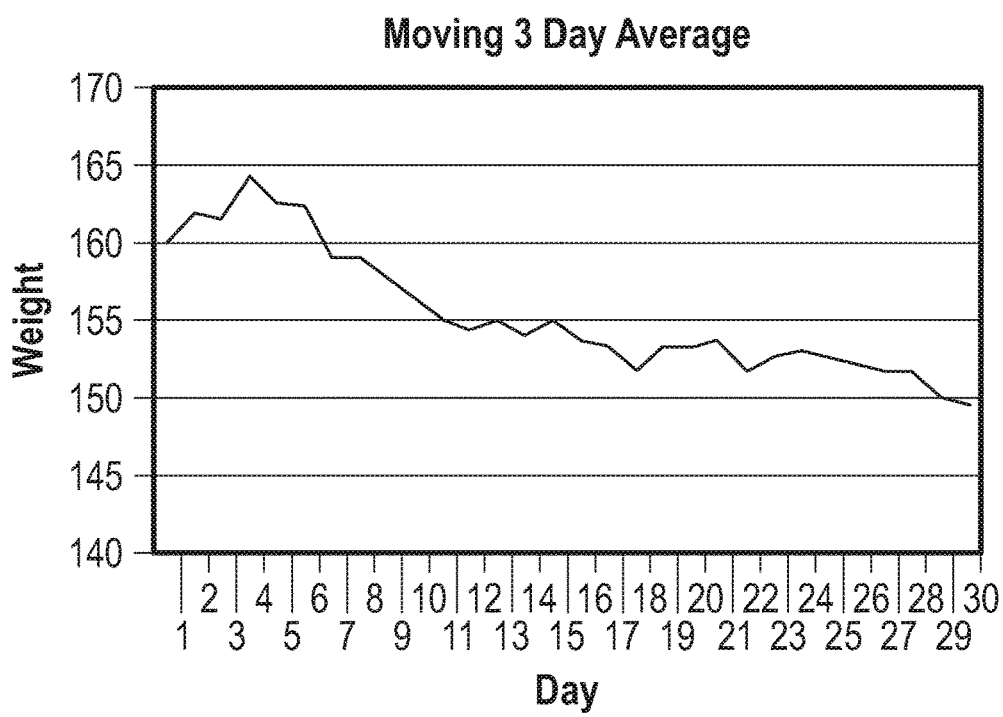
FIG. 10B is a graph showing the data of FIG. 10A smoothed as a moving 3-day average.

In some embodiments, the weight management systems described herein can be configured to smooth weight measurements to avoid stress associated with small changes in weight. Referring to FIGS. 9A-9B, a person with anorexia nervosa may need to gain ten pounds over the course of a month to move into a healthy weight range. Referring to FIG. 9A, the weight measured each day is likely to fluctuate, and presenting this to a user may cause an adverse reaction, even if the weight is converted to a color, because it may show periods of weight loss and gain. Instead, as shown in FIG. 9B, the weight measurement can be smoothed over several measurements using a variety of techniques, such as a three-day moving average. That smoothed weight can then be converted to non-numerical output. As a result, the user can avoid receiving feedback caused by fluctuating weight measurements and can rather obtain feedback related to his or her general weight trend. In some embodiments, the smoothed weight can also be used to better assess the rate of weight change over time. As another example, referring to FIGS. 10A and 10B, an individual may have a goal to decrease his or her weight by 10 pounds over the course of one month. If measurements are taken each day, the raw data (shown in FIG. 10A) will show fluctuations while the smoothed data (shown in FIG. 10B) will show the general trend. The smoothed data can then be used to provide non-numerical feedback to the user.

Many elements of the weight management systems described herein can be customized, including, but not limited to: the goals, health needs, medical history, pictures to be displayed, sounds and music to be played, words of inspiration to be displayed, colors for feedback, how blended colors are, phone number for feedback, people on team and what information they are authorized to receive and send, frequency at which weight is measured, whether results are reported immediately or delayed, by how much time the reporting is delayed, whether weight measurements should be smoothed over time, goal weight zone, time duration for goal attainment, weekly goals, monthly goals, final goal, frequency of reports to user, whether numerical measurements are reported to the user, which team members get numerical information, whether there are alerts, thresholds for alerts, and who receives them. Default sets of customized parameters can be created to enable quick set up.

Figure 5A:
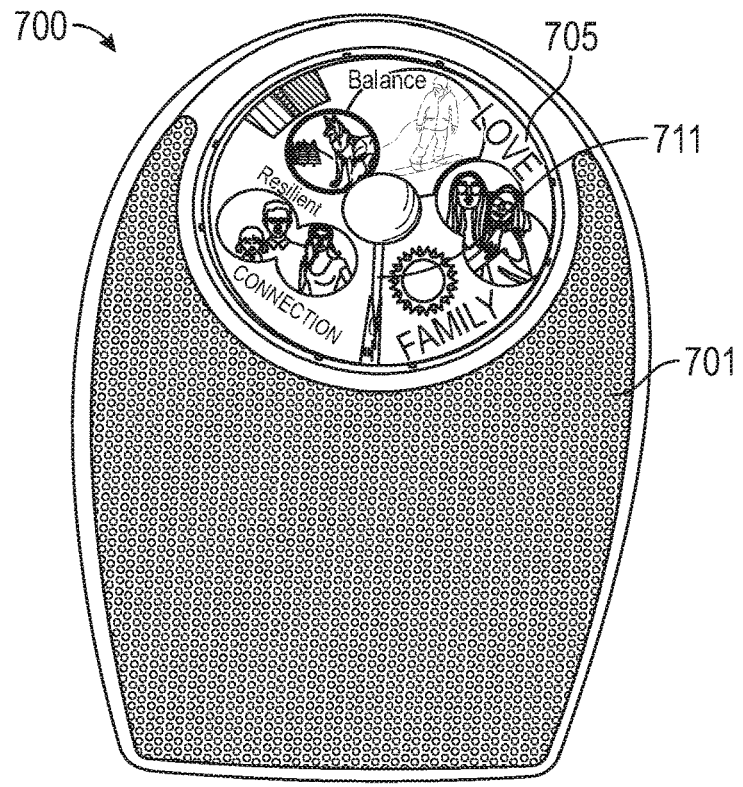
FIG. 5A shows an exemplary weight management system as described herein.
Figure 5B:
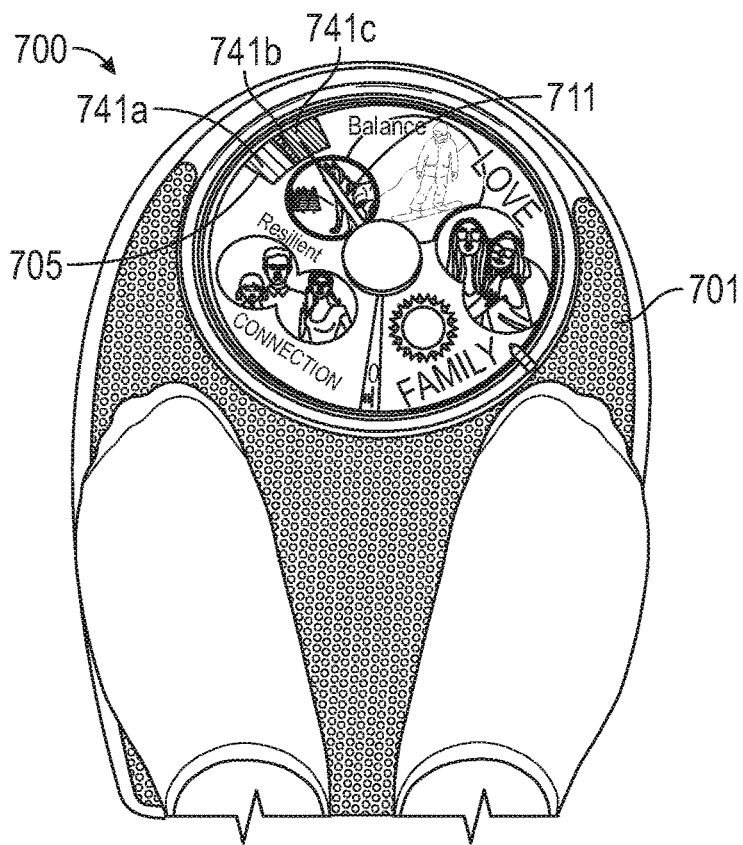
FIGS. 5B-5D show a user standing on the exemplary weight management system of FIG. 5A.
Figure 5C:
Figure 5D:
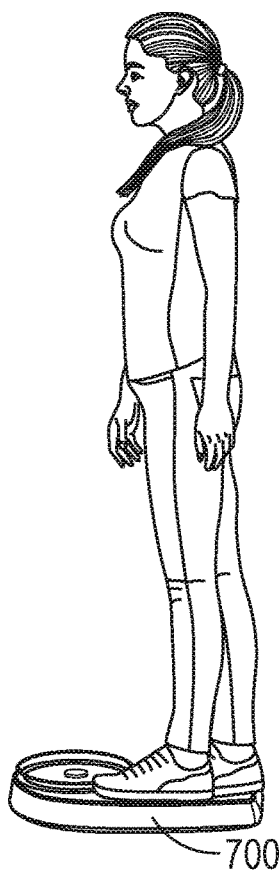
Figure 5E:
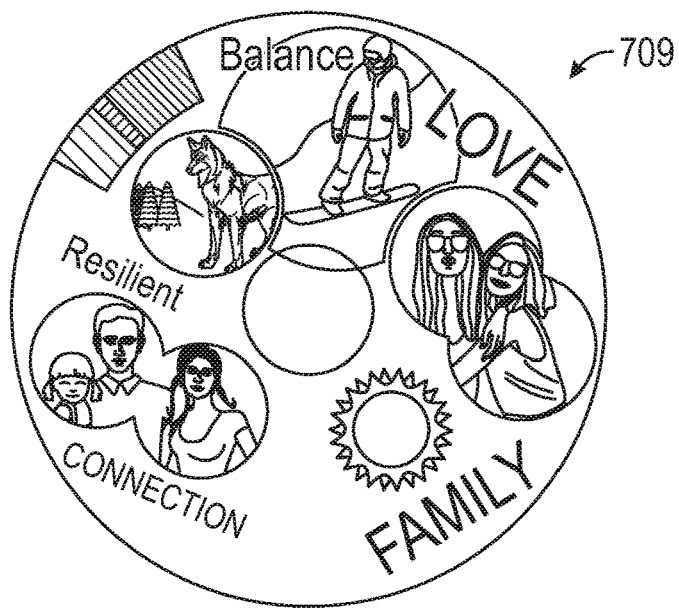
FIG. 5E shows the converter of the exemplary weight management system of FIG. 5A.

Referring to FIGS. 5A-5E, in some embodiments, the weight management system can be personalized or customized with can include user selected words of affirmation, quotes, photos, music, sound, video and art that makes them feel supported and motivated. For example, system 700 includes a display 705 that is retrofitted onto a pre-existing analog scale that includes a platform 701 and the weight sensor. The display 705 includes the user's pictures and words of inspiration. As shown in FIG. 5A, when the user is not on the platform 701, the indicator 711 can be at a neutral or zero position. Referring to FIG. 5B, when the user steps on the platform 401, the indicator 711 can move to provide non-numerical feedback regarding the user's weight (FIG. 5B shows the indicator on zone 741c of display 705). The customization can provide a positive mindset to the user as the weight measurement is taken (shown in FIGS. 5C and 5D). Referring to FIG. 5E, in some embodiments, users may submit their photos, sounds, voices, music, and personalized messages through a website; these customizations can then be incorporated into the weight management system (e.g., through converter 709 that can function as part of display 705). Users may use pre-designed images, sounds, music, and word-art to have on their weight management system. Some of the words include but are not limited to "family," "connection," "love," "resilient," "beautiful," and "balance." The images, sounds, music, and words are displayed and can be independent of the weight measurements and provide a positive context for the measurement.

Figure 6:
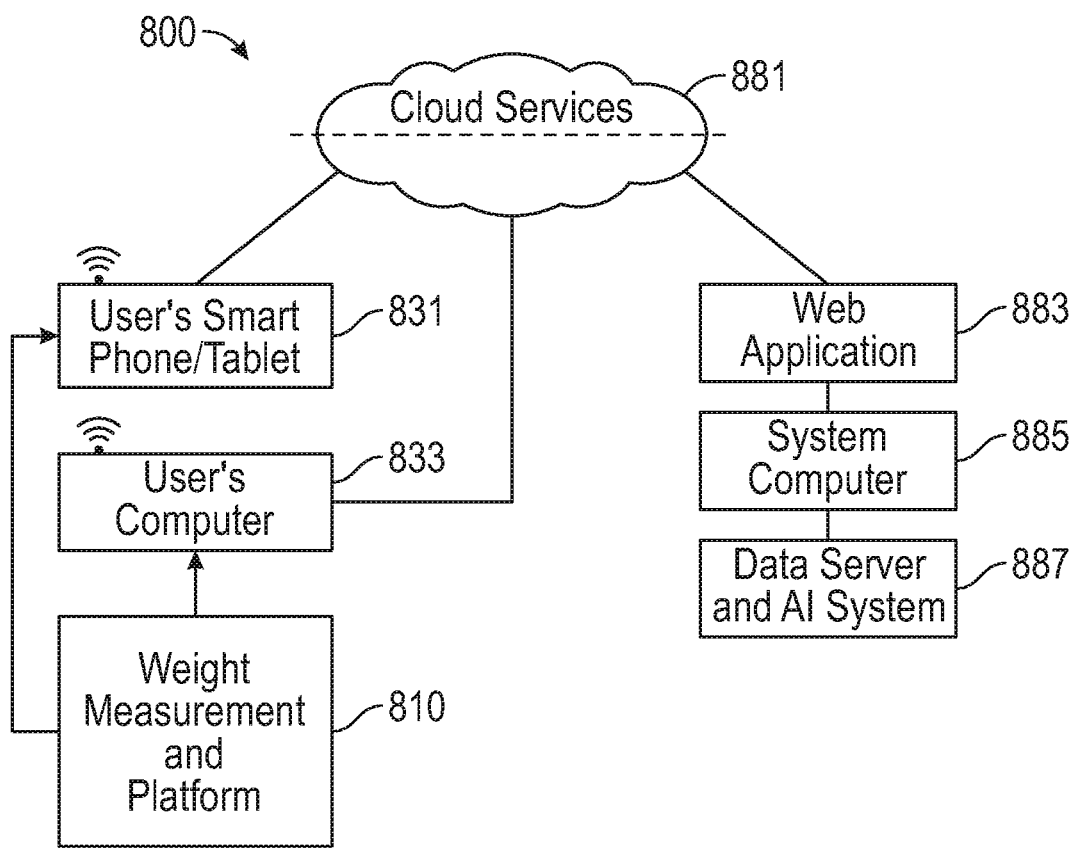
FIG. 6 is a system diagram of an exemplary weight management system as described herein.

Referring to FIG. 6, in some embodiments, an app 831 or personal computer 833 of the weight management system 800 can be used to provide personalized or customized sounds, words, colors other non-numerical information regarding the user's weight (obtained from unit 810). Further, these customizations may change over time via input from the user or via an algorithm. Additionally, in some embodiments, the 831 or personal computer 833 can be connected through the cloud 881 to a web application 883, system computer 885, and/or data server 887 and artificial intelligence system. When the unit 810 can be remotely connected to such devices and systems, the weight information or non-numerical feedback can be delivered immediately at the time of measurement or it can be delayed for a set period of time. For example, the weight measurement can be taken and the feedback provided 1 minute or more, 1 hour or more, 4 hours or more, 8 hours or more, or 12 hours or more after the weight measurement. Further, in some embodiments, feedback might only be delivered at set times. For example, an individual may step on a scale every day but only receive feedback once per week. Providing such delayed feedback can advantageously reduce the stress associated with taking weight measurements.

Figure 13:
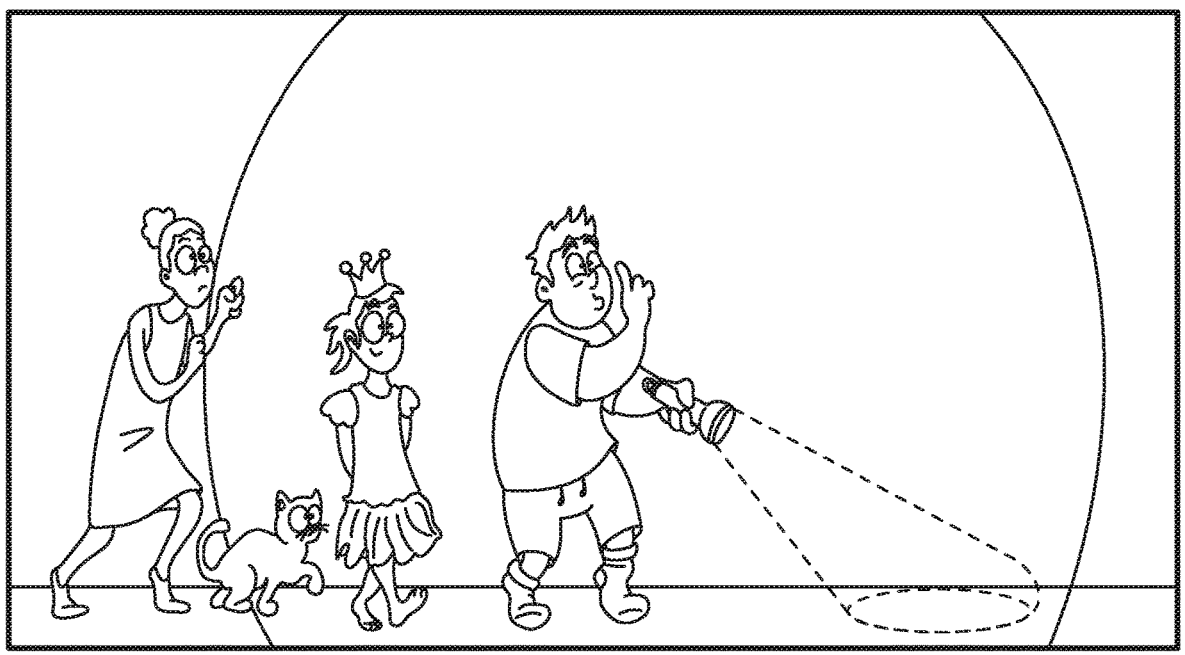
FIG. 13 shows an exemplary visual narrative that can be used to provide non-numerical feedback as part of a weight management system.

Referring to FIG. 13, in some embodiments, visual narratives can be used to generate curiosity and engagement with the weight management system. For example, if a user desires to gain weight for recovery from an eating disorder, the user can navigate through a graphical story based on their weight measurements. The story can progress each time the weight management system is used. The user may not receive numerical feedback of his or her weight, but may instead observe a character move forward in the story, which provides qualitative feedback on their progress. This story can be customized based on user's engagement with their device and/or the progress of the user toward their health goals. The weight management systems described herein can include a variety of stories, characters, and graphical elements that may be personalized.

In some embodiments, users can select the kind of feedback he or she receives. For example, the user can choose to view non-numerical weight information on a scale of colors to represent where he or she is that day relative to their goal. The user can choose to have the non-numerical weight displayed through a positive image or single color that represents if he or she is in a healthy zone or not. In some embodiments, it is also possible to customize whether a marker is used that shows the current weight on a color scale (such as shown in 11A) or just the color (such as shown in 11B). This is important because the display shown in FIG. 11A provides more quantitative information than the display shown in FIG. 11B, and one may be more helpful than the other depending on the user's condition and goal. In some embodiments, users can opt to have his or her weight tracked over time with display schemes based on weekly or monthly trends.

The personalization of a user's desired weight range and weight trend can be incorporated into the weight management system through several different mechanisms. Prior to the initial use of the weight management system, an individual or their doctor, dietician, family member, or another person can complete a form that specifies their goals, target weight ranges, optional medical history, and other information. A dietician, physician, or algorithm may optionally review this form to account for factors that may affect an individual's weight management plan. For users who need to gain or lose weight, a physician or algorithm may optionally make suggestions regarding approximately what progress should be expected, such has how much weight loss or gain can be expected each week; this information is used to set individualized time-varying goals. These goals can be set based on previous analyses of large data sets to optimize goal attainment. In some embodiments, the weight management system can alert the user if a height and weight combination is entered that corresponds to an unhealthy body mass index (BMI). This system of alerts will optionally direct users to a support system to discuss why the unhealthy weight range was selected. To assure that a user is able to create a weight management system that best supports them, the weight management system can enable interaction with a customization tool through the weight management system set up process.

Figure 7:
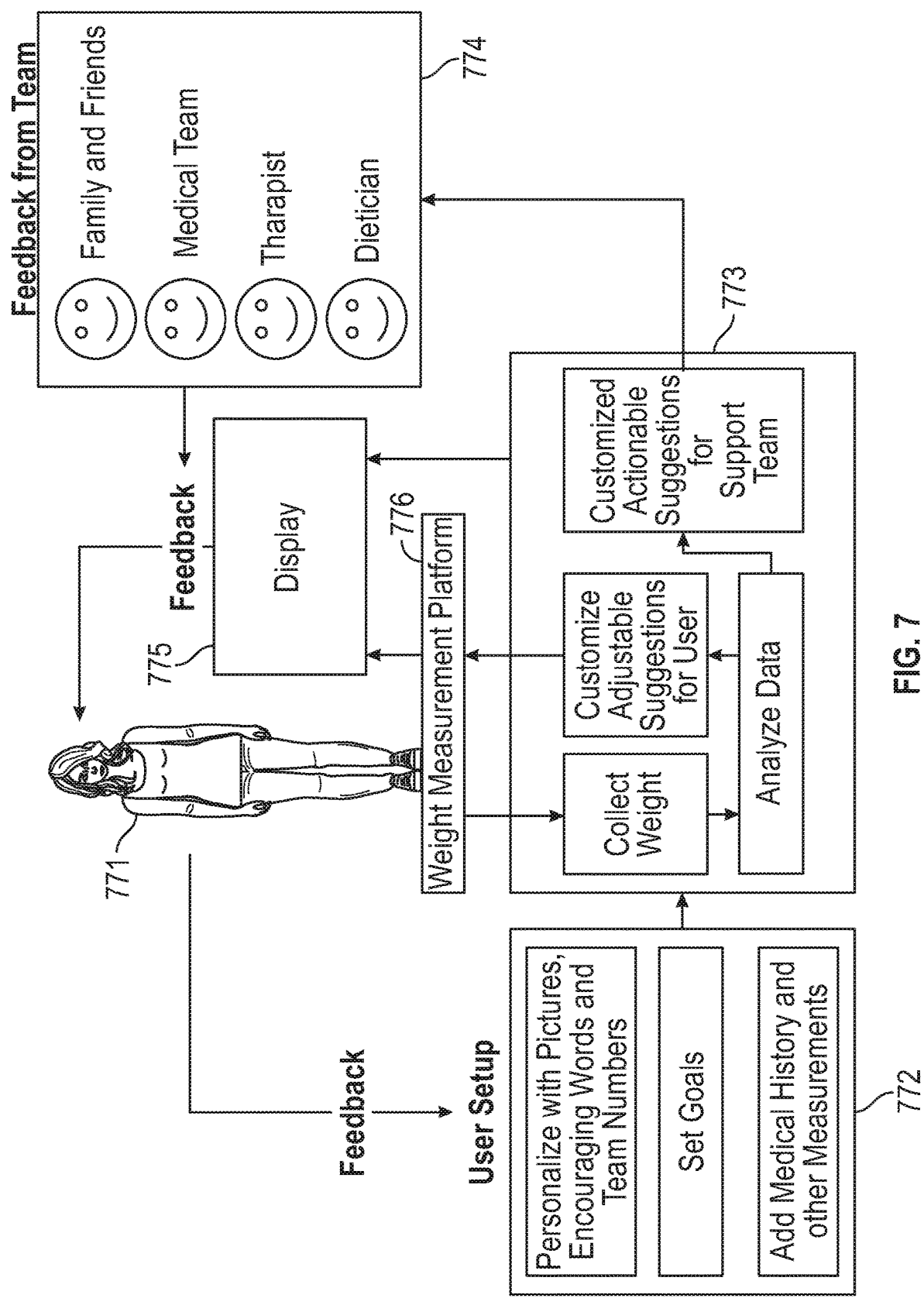
FIG. 7 is a system diagram showing use of an exemplary weight management system.

An exemplary flow diagram of a weight management system as described herein is shown in FIG. 7. The user 771 can provide user setup 772 for the system, which can include personalization with pictures and encouraging words and information regarding the team members, user goals (e.g., weight goals), medical history, and other measurements. The user setup 772 can be fed to the controller 773, which can have a machine learning engine based on dietary, therapeutic, and medical knowledge, data from users and other databases, and/or a behavior model. The controller 773 can be configured to act as the converter to analyze and convert measurements taken from the weight measurement platform 776 to non-numerical output based on the user set up 772 and information stored in its learning engine. The controller 773 can further be configured to provide customized adjustable suggestions for the user 771 and/or actionable suggestions for the support team 774. The information from the controller 773 can be provided to the team 774 and/or can be provided directly to the user 771 as non-numerical feedback 775 including a supportive message, a story storyline, sounds, colors, or other supportive feedback. Some of this feedback can be dependent to the current and past measurements, whereas other feedback can independent of the current and past measurements. For example, the color feedback can be dependent on the current and past measurements, whereas text messages to promote a positive mind set and favorite pictures and phrases may be independent of current and past measurements.

Figure 8:
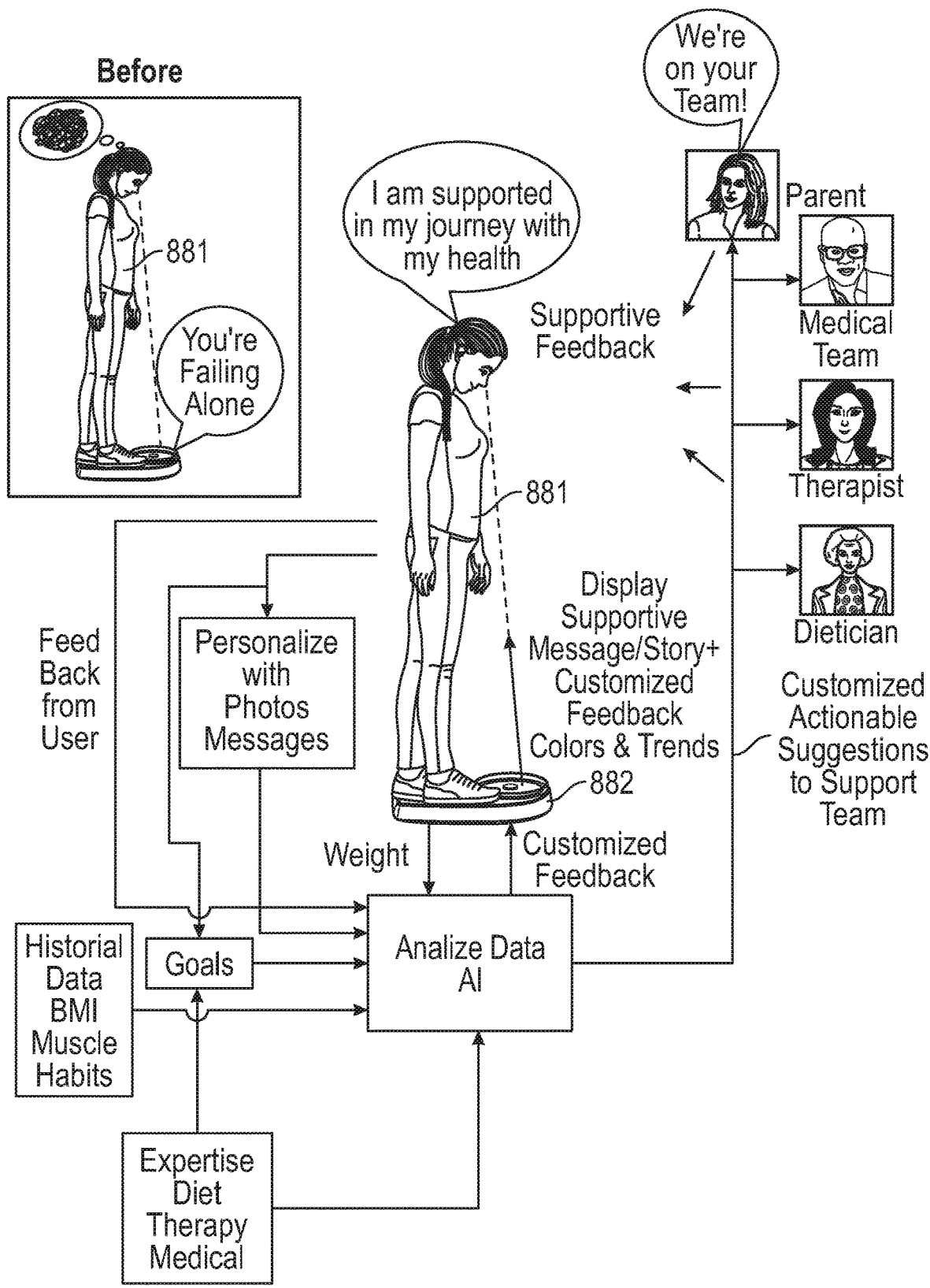
FIG. 8 is another a system diagram showing use of an exemplary weight management system.

A similar exemplary flow diagram of a weight management system as described herein is shown in FIG. 8. Before use of the system, the user 881 might feel alone and be suffering from obsessive thoughts about weight. In contrast, when the user 881 steps on the platform 882, he or she can feel supported by non-numerical feedback from the display, music, and/or from parents, medical teams, therapists, dietitians, and/or anyone else with access to the weight management system. Additionally, the personalized aspects of the system can help the user 881 maintain a positive mindset. The system can provide customized actionable feedback to the user and to the support team. The user can provide feedback on how the use of the system is affecting them, and the system can adjust to provide a more positive experience.

In some embodiments, the weight management systems described herein thus can include a social network to support users. Many individuals have negative experiences with scales, their weight, or their body image. The weight management systems described herein therefore can advantageously include a support community, including a variety of support options. For example, a user may be able to request a mentor through the weight management system. Mentors may be people who are experienced using their weight management system, are willing to offer support, and are matched with the user via a matching algorithm. As another example, a user may be able to apply for a buddy through the weight management system. When individuals apply for a buddy, they can fill out a questionnaire, and the weight management system then connects two applicants that can best support each other through a matching algorithm. In some embodiments, the weight management systems described herein can include a support forum for users to converse about difficult topics, receive and give support, and ask questions via their weight management system or associated app. To ensure the forums are used to promote the recovery and health, algorithms or humans can monitor the forums.

In one embodiment, the weight management systems described herein can be equipped with the ability to call or accept calls from desired contacts, avoiding the alone feeling people have when they step onto their scale. In one embodiment, friends, family, and others can submit voice messages, video recordings, words of affirmation, and/or pictures to be shown to users when they step on the weight management system. In one embodiment, support people can be notified automatically when a user steps on to the weight management system so that they can contact the user to offer support. The weight management system can also provide information and coaching for friends and family members so that they learn and are reminded of the types of messages that are helpful. An automated support voice may also be used to provide support, building a positive connection with the user. This can help users feel supported and connected even if they are by themselves when using the weight management system. Further, the weight management systems can implement compassionate communication as a way to give automated feedback when goals are being met and not being met. The weight management systems can learn a "personality" that connects to its user and support their health goals in an automated means or using feedback from the user.

In some embodiments, the user's response to the non-numerical feedback can be measured so that the feedback adapts to best achieve the user's health goals and promotes a positive mindset. Data on the type feedback and responses can be incorporated into a computational behavioral model to optimally adapt the feedback.

Advantageously, the weight management systems described herein can utilize the power of mindsets, psychological lenses through which individuals view their health and behavior. Mindsets are powerful and can alter oxygen consumption, athletic performance, and gut metabolism. Most scales and health apps fail to adequately support their users because they merely provide data feedback and set arbitrary goals, which can discourage users and evoke negative mindsets. In contrast, the weight management systems described herein provide information to users to evoke a positive mindset. The use of a weight management system, such as system 100, 200, and 300 can reduce the stress, anxiety, and obsessions associated with weight measurements and can reduce the difficulty in weight management. Referring to FIG. 12, data was gathered for a prototype weight management system as described herein when used over a 3-month period for an individual with anorexia nervosa using the following survey:

What is your level of stress associated with measurement of weight on a traditional numerical scale? (0=no stress, 10=extremely stressful)

What is your level of stress associated with measurement of weight on the prototype weight management system (0=no stress, 10=extremely stressful)

What is your level of anxiety associated with measurement of weight on a traditional numerical scale? (0=no anxiety, 10=extremely anxious)

What is your level of anxiety associated with measurement of weight on the prototype weight management system (0=no anxiety, 10=extremely anxious)

How does management of weight on a traditional scale influence your OCD? (0=does not trigger obsessions, 10=immediately triggers strong obsessions)

How does management of weight on the prototype weight management system influence your OCD? (0=does not trigger obsessions, 10=immediately triggers strong obsessions)

How does management of weight on a traditional scale influence your OCD? (0=does not trigger compulsions, 10=immediately triggers compulsions)

How does management of weight on the prototype weight management system influence your OCD? (0=does not trigger compulsions, 10=immediately triggers compulsions)

How do you rate your difficulty in managing your weight for a 3-month period with a traditional scale? (0=easily able to manage weight, 10=completely unable to manage weight)

How do you rate your difficulty in managing your weight for a 3-month period with the prototype weight management system? (0=easily able to manage weight, 10=completely unable to manage weight)

As shown in FIG. 12, the prototype weight management system produced lower stress, lower anxiety, reduced obsession, reduced compulsions and greater ease with weight management over a 3-month period relative to a traditional scale. In some embodiments, the stress, anxiety, obsession, compulsions, and difficulty associated with weight management can be reduced by 2-10 times, such as 3-8 times, such as 4-6 times. The large differences in in stress, anxiety, obsession, compulsion, and difficulty associated with the weight management system can advantageously correlate with measurable differences in the physiology measured in terms of changes in heart rate, blood pressure, sweat, and other measurements of stress and anxiety.

In one embodiment, the mindset of users interested in weight loss can be made more positive by providing educational information demonstrating that their daily activity is valuable exercise that contributes to their health. In another embodiment, the mindset of users needing to gain weight can be made more positive by informing them that their nourishment will help quiet their mind and bring joy to life.

In some embodiments described herein, non-numerical feedback that is unrelated to the weight measurement can be used in addition to or instead of non-numerical feedback that is related to the weight measurement. For example, the weight management systems described herein can incorporate calm, positive reinforcement, such as "your recovery is proceeding well." Other example messages to evoke a positive mindset about health and adequacy that can be incorporated into the weight management systems described herein include: "Meeting your goals will give you greater vitality"; "Your body is able to help you meet this challenge"; "This is a challenge you can manage"; "This challenge allows you to discover more meaning in life"; "This challenge can make you stronger"; and "Meeting your goals will be beneficial to your health." These messages to evoke a positive mindset can be provided regardless of the weight measurement that is obtained. Similar non-numerical feedback that is unrelated to the weight management can include sounds, music, photographs, or other elements intended to provide a positive mindset. This information can be provided to the user with or without information related to current or past measurements.

In some embodiments, the weight management systems described herein can be used to monitor the weight of multiple individuals. In one embodiment, the weight management systems described herein include a foot scanner to identify the individual and/or to adjust the display to show the specific individual's healthy zones and progress.

In one embodiment, the weight management systems described herein include an adjustable system to promote a healthy weight trend for people who need to gain or lose weight. During weight restoration, people typically gain or lose 1-4 pounds per week. A dietician, physician, caregiver, or algorithm can program the weight management system such that it shifts the desired zones can according to the healthy trend of the individual's weight. Each day or week (depending on how often the individual is weighed), an individual's desired zone can move up or down to match his or her time-dependent goal weight. The individual can see that he or she is increasing his or her health (whether that means weight gain, maintenance, or loss). These adjustments can be made via a user, health professional, algorithm, or other means. The goals may be optimized based on analysis of large datasets to improve goal attainment.

The weight management systems described herein can be used for weight management and/or treatment of a variety of individuals.

In some embodiments, the weight management systems described herein can be used for weight loss. The weight management systems can thus be used to motivate users to lose weight without having to focus on the specific numbers. The weight management systems can encourage a healthy balanced life. The weight management systems can be programmed to show how to lose weight healthfully, and the user can see what is working without becoming anxious or obsessed each day about a number.

In one specific embodiment, the weight management systems described herein can be used to treat individuals with congestive heart failure (CHF). Individuals with CHF generally need to track their weight diligently, and many patients are required to weigh themselves daily. Rapid weight gain for individuals with CHF is a sign that their condition has worsened and that they need immediate medical attention. The weight management systems described herein can therefore include established thresholds for weight-gain and rate of weight gain for one or more individuals with CHF. If either of these thresholds is exceeded, the weight management system can alert the user and/or care givers. Advantageously, the weight management system may not display the user's weight, thereby protecting the user from the negative mental and emotional side effects that can occur as a result of knowing the numerical weight to value. In some embodiments, the weight management system can provide qualitative information to the user while transmitting the numerical value of the weight to the user's physician or other members of their treatment team who may require quantitative information. In some embodiments, the weight management systems described herein can be used to monitor weight every day at the same time and to detect any sudden change in weight. In some embodiments, the weight measurements obtained by the weight management systems when used for treatment of CHF are not smoothed so as to identify even small changes in a short period of time, which can be dangerous for a patient with CHF.

Figure 14:
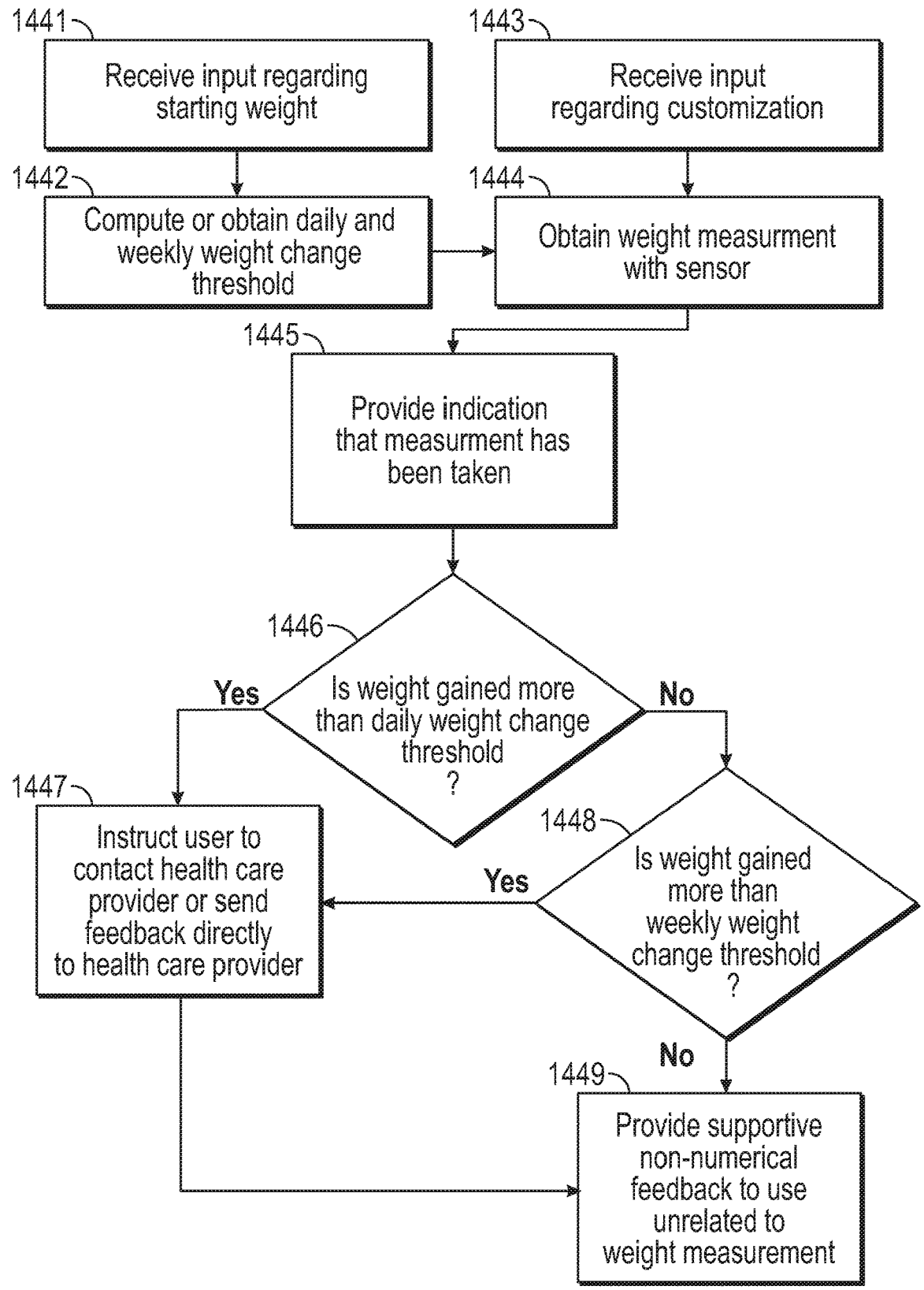
FIG. 14 is a flow chart showing an exemplary method of use of a weight management system to treat congestive heart failure.

An exemplary flow chart for treatment of congestive heart failure with the weight management system described herein is shown in FIG. 14. At step 1441, the weight management system receives input regarding the CHF patient's starting weight. In some embodiments, this weight can be taken at the hospital on the day of discharge. At step 1442, the daily and weekly weight change thresholds for the patient can be computed or obtained (for example, the daily weight threshold might be a weight gain of 2-3 pounds in 24 hours). At step 1443, customization can be provided by the patient, including inspirational words, pictures, music, voices, videos, and/or information regarding the users treatment team and support network. At step 1444, the patient's weight measurement can be obtained with the weight sensor of the device (e.g., by having the user stand on a platform of the weight management system). At step 1445, the weight management system can provide an indication (such as a sound or other immediate feedback) that the weight measurement has been taken without displaying the numerical value of the weight. At step 1446, it can be determined whether the weight gained in one day is more than the daily weight change threshold (i.e., relative to the previous days measurement). If the weight gained in one day is more than the daily weight change threshold, then at step 1447, the weight management system can instruct the user to call his or her healthcare provider and/or can send feedback directly to the healthcare provider. If weight gain is not more than the daily weight change threshold, then at step 1448, it can be determined whether the weight gained is more than the weekly weight change threshold. If the weight gained is more than the weekly change threshold, then the weight management system at step 1447 can instruct the user to call his or her healthcare provider and/or send feedback directly to the healthcare provider. If the weekly weight gained is not more than the weekly change threshold or after the user has been instructed to contact the healthcare provider or feedback is sent directly to the healthcare provider at step 1447, then the user at step 1449 can be provided with non-numerical supportive feedback that is related to the wheat measurement. Such non-numerical supportive feedback that is unrelated to the measurement could be, for example, a written message, voice, text, sound, music, or other means to help establish a healthy mindset and maintain engagement with the CHF treatment. In some embodiments, the user can be reminded on a regular basis (e.g. at the same time every day) to use the weight management system. In some embodiments, the weight management system can request feedback on the user's experience to provide data for further customization.

The requirement for regular weight measurements that occurs for patients with CHF can be discouraging and anxiety provoking. The weight management systems described herein can enable patients with CHF to monitor their weight while reducing the negative emotional valance associated with stepping on a scale. Advantageously, the user may not have to worry about receiving a daunting number regularly (e.g., every morning) that may negatively influence the user emotionally or mentally (e.g., for the rest of their day). Additionally, the weight management system can improve the CHF user's relationship with their treatment. That is, when a patient feels more positive about their treatment, he or she is more likely to engage and feel hopeful regarding the treatment process. This positive mindset can have powerful beneficial effects on the outcome of treatments, much like the potent placebo effect.

In another specific embodiment, the weight management systems described herein can be used to treat individuals with one or more eating disorders, such as anorexia nervosa. Individuals suffering from anorexia nervosa generally experience weight loss and need to gain weight to recover from his or her illness. Once weight has been restored to a healthy range, individuals need to maintain their weight within this range. Many people with anorexia nervosa become obsessed with weight loss and may be profoundly upset with knowing his or her weight during recovery. As a result, such individuals frequently rely on others to monitor their weight, limiting their ability to participate fully in their recovery. The weight management systems described herein advantageously provide a means to reveal qualitative and supportive information to the individual with anorexia nervosa while also providing quantitative information to their treatment team.

Figure 15:
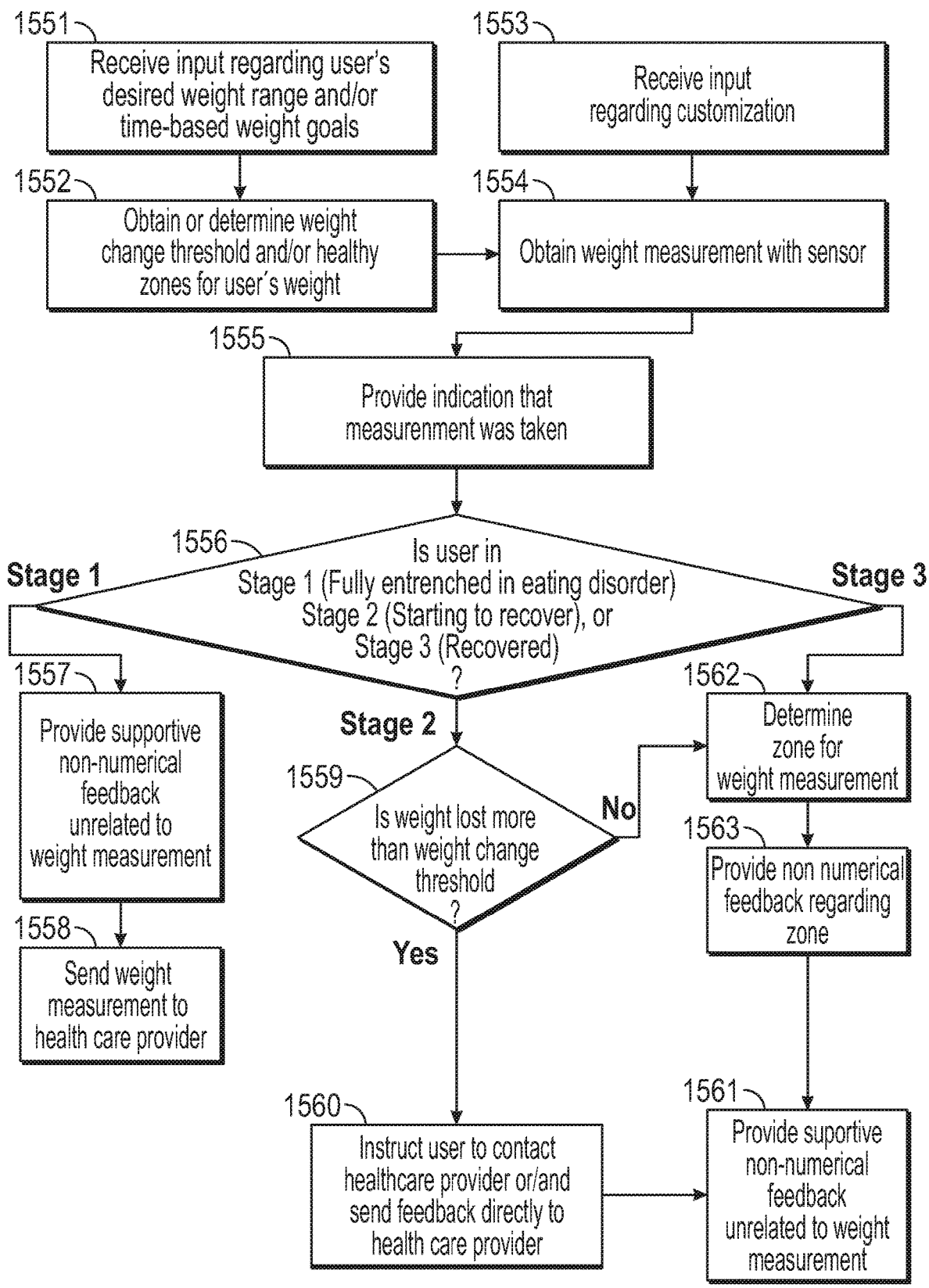
FIG. 15 is a flow chart showing an exemplary method of use of a weight management system to treat anorexia nervosa.

An exemplary flowchart for the treatment of anorexia nervosa using a weight management system as described herein is shown in FIG. 15. At step 1551, the weight management system can receive input regarding the user's desired weight range and/or time based weight goals. This input can be made by the user, a health professional, or an algorithm. In one embodiment, the desired weight range and/or time based weight goals can be optimized based on the analysis of large data sets to improve goal attainment. Data from scientific literature regarding feasible weight gain rate along with data collected by the weight management system can be incorporated into a computational behavioral model to guide users and their support team to establish optimal goals. At step 1552, the weight management system can obtain or determine weight change thresholds and/or healthy zones for the user's weight. At step 1553, the weight management system can receive input regarding customization specific to the user. Such customization can include, for example, inspirational words, pictures, music, voices, videos, and/or a listing of individuals who are part of the user's treatment team. The customization can also include specification of which members of the treatment team will receive quantitative information and what type of information will be provided. At step 1554, the weight management system can obtain a weight measurement with a measurement sensor (e.g., from the user stepping on a platform of the weight management system). At step 1555, an indication that a measurement was taken can be provided without providing numerical information regarding the measured weight. In some embodiments, the indication can be visual, voices, music, or positive feedback that may take attention away from the measurement. At step 1556, it can be determined whether the user is in stage 1 of the treatment process (i.e., is fully entrenched in the eating disorder), stage 2 of the treatment process (i.e., starting to recover), or a stage 3 of the treatment process (recovering and in need of maintaining healthy weight). If the user is in stage 1, then at step 1557, the weight management system can provide supportive non-numerical feedback that is unrelated to the weight measurement. Such non-numerical feedback that is unrelated to the weight measurement can be, for example, messages to shape a positive mindset and encourage the user's engagement in their recovery. Additionally, the numerical weight measurement can be sent to the healthcare provider at step 1558. In some embodiments, if the user is in stage 1, then the weight management system can prevent a measurement from being taken more than a set number of times per day (for example, the measurement can only be taken once per day). If the user is in stage 2, then it can be determined at step 1559 whether the weight lost is more than the weight change threshold. If the weight lost is more than the weight change threshold, then the weight management system can, at step 1560, instruct the user to contact a healthcare provider or can send feedback directly to the healthcare provider and, at step 1561, can provide supportive non-numerical feedback to the user that is unrelated to the weight measurement. If at step 1559, the weight lost is not more than the weight change threshold, then the weight management system can at step 1562 determine a zone for the current weight measurement and at step 1563 provide non-numerical feedback regarding the zone. Additionally, the weight management system can provide supportive non-numerical feedback that is unrelated to the weight measurement to the user at step 1561. The use of the weight management system in stage 2 can be used to encourage the user's engagement in his or her own health and recovery. In some embodiments, at step 1562 and 1563 for Stage 2, the weight measurement from the current day can be combined with measurements from previous days to use a smoothing function to remove small variations in weight prior to feedback. The feedback (e.g., color) can be smoothed and this smoothed feedback can be provided to that user. This feedback may be delivered immediately or at a later time, depending on the user's preference. The feedback can still be based on progress (relative to previous measurements) and engagement and not on current weight relative to their ultimate healthy weight range. Finally, if it is determined at step 1556 that the user is in stage 3, then at step 1562, the weight management system can determine the zone for the current measurement and at step 1563 can provide non-numerical feedback regarding the zone. In this case, supportive non-numerical feedback unrelated to the weight measurement can also be provided at step 1561. The weight management system in stage 3 can be used to help the user maintain his or her healthy body weight. In one embodiment, if the user is within his or her healthy range, he or she can be given feedback that he or she is in the healthy range (e.g., via colors or a text message). If the user is below the healthy range by a less than a threshold amount, he or she can be given feedback that he or she is slightly below the healthy range and that he or she may want to consider increasing nutritional intake and reducing physical activity until the healthy zone is achieved. If the user is below the healthy range by more than a small threshold, then he or she can be given feedback that he or she is well below their healthy range and that he or she may want to work hard to increase nutritional intake, reduce physical activity, and/or reach out to others for support.

When a patient with anorexia nervosa is far enough along in recovery to be accountable for their weight, using a numerical scale can trigger a relapse. The weight management systems described herein advantageously allow individuals to take accountability for their health and recovery while avoiding a trigger that may create a relapse. The qualitative display helps patients with anorexia and other eating disorders to distance themselves from the obsession with weight and to be more flexible about eating and thinking about eating, an essential element of recovery.

Further, physicians and others caring for an individual with anorexia nervosa or other eating disorder often need quantitative information, such as weight to a resolution of 0.2 kg, to properly monitor the weight of an individual. The weight management systems described herein can register and store this quantitative information and/or connect to an app, transmitting the information to a smartphone used by a dietician, physician, or other person.

In another specific embodiment, the weight management systems described can be used to support athletes during training. That is, coaches and rules of competition frequently demand athletes to maintain a particular weight. Wrestlers, boxers, and martial artists, for example, compete in their weight ranges, and athletes of these sports spend much of their time tracking and monitoring their weight. Additionally, many endurance athletes need to make sure that they are consuming enough nutrition to support their heath and provide energy to fuel their training regime. Many distance runners suffer stress fractures, in part because they enter a state of negative energy balance in which they are not consuming sufficient calories to maintain their weight. The weight management systems described herein can help decrease stress fractures among athletes by supporting proper nourishment. Similarly, certain sports have high pressures to be small and thin. For example, performance in sports such as dance and gymnastics is enhanced by low body weight. The people who succeed in these sports tend to have a naturally small build, but there is intense pressure to maintain a small figure. These athletes need to maintain a healthy weight to perform. Individual athletes often take on the burden of worrying about their weight. This can distract them from training and ultimately decrease their performance, psychological well-being, and lead to disordered eating. Further, it is easy for athletes to become obsessed with a numerical weight, and athletes may become hyper-focused on small changes in weight. The weight management systems described herein can resolve this problem by conveying sufficiently quantitative information to the athlete while avoiding numerical weight measurements when they might be detrimental.

Figure 16:
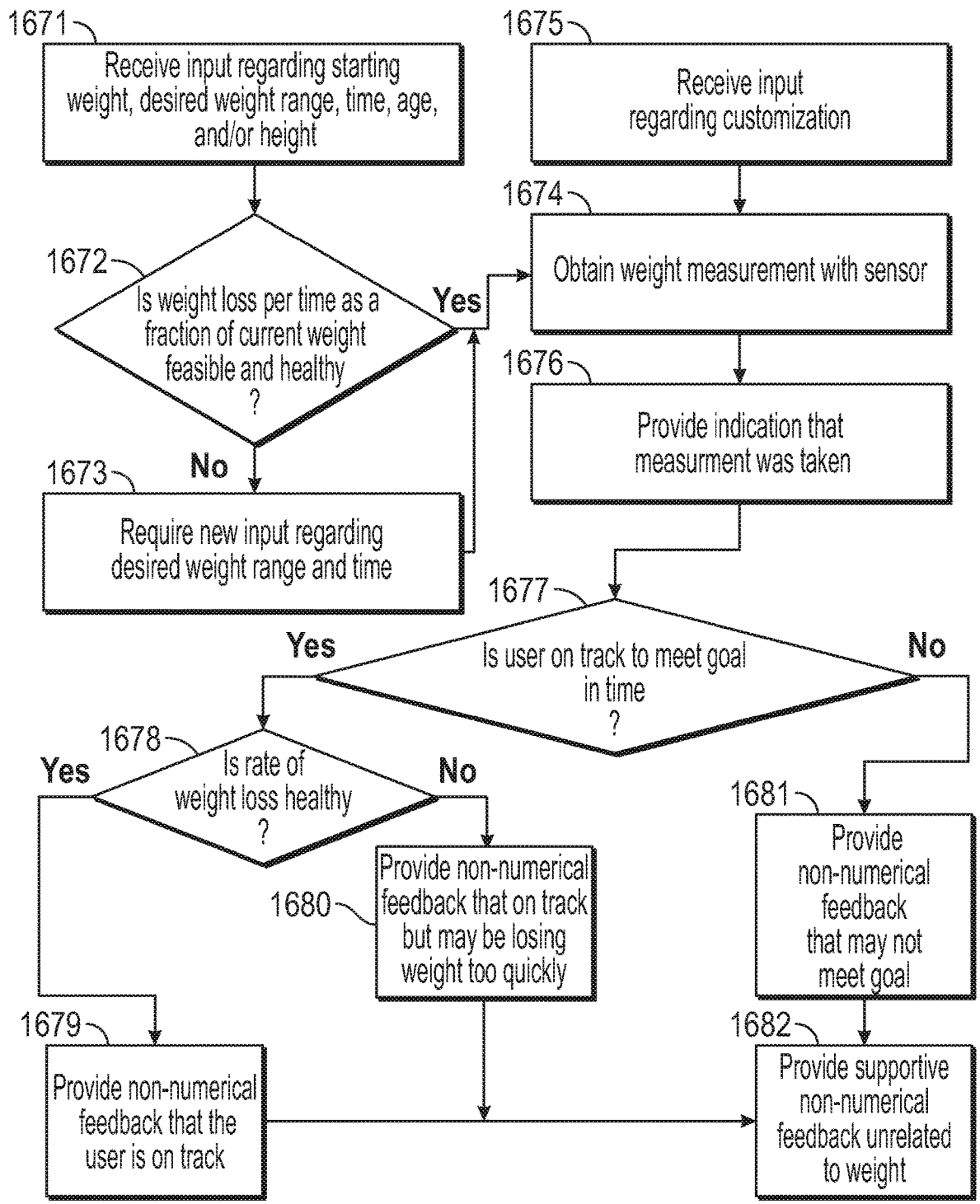
FIG. 16 is a flow chart showing an exemplary method of use of a weight management system for athletes.

An exemplary flowchart for the method of supporting an athlete who needs to lose weight with a weight management system described herein is shown in FIG. 16. At step 1675, the weight management system can receive input regarding customization from the user. At step 1671, the weight management system can receive input regarding the starting weight, desired weight range, time to meet the goal, and age and/or height of the user. At step 1672, it can be determined whether the weight loss per time as a fraction of current weight is feasible and healthy. At step 1673, if the weight loss per time as a fraction of current weight is not feasible and healthy, then the weight management system can require a new input regarding desired weight range and time. After the new input is provided at step 1673 or if the weight loss per time is a fraction of current weight is feasible and healthy at step 1672, then at step 1674 the weight management system can obtain a weight measurement with the sensor (e.g., after the user steps on the platform of the health maintenance system). At step 1676, the weight management system can provide an indication of the measurement was taken without providing the numerical weight value. At step 1677, it can be to be determined whether the user is on track to meet the goal in the specified time. If the user is on track to meet the goal in time, then at step 1678, it can be determined whether the rate of weight loss is healthy. If the rate of weight loss is healthy, then at step 1679 the weight management system can provide non-numerical feedback that the user is on track to meet the goal. If the rate of weight loss is not healthy at step 1678, then the weight management system can provide at step 1680 non-numerical feedback indicating that the user is on track, but may be losing weight too quickly. If at step 1677, the user is not on track to meet the goal in time, then the user can be provided at step 1681 with non-numerical feedback that he or she may not meet the set goal. At step 1682, non-numerical supportive feedback can be provided in all cases that is unrelated to the users measured weight. In some embodiments, the athlete's coach or healthcare providers may be provided with numerical information regarding the athlete's weight.

In some embodiments, the weight management system may be used for athletes who are trying to maintain their weight. In such a case, the steps can be similar to the steps of stage 3 of the flowchart of FIG. 15. That is, the weight management system can obtain input regarding the starting weight, desired weight range, time to achieve the goal, age, and height. The weight management system can further obtain input regarding customization. The user can stand on a platform, and the sensor can be used to measure weight. By default, the weight may not be displayed to the user, but a sound or other immediate feedback lets the user know that the weight has been measured. The converter can then information from the current measurement along with the input to determine the type of feedback delivered to the user. If the user is within his or her healthy range (e.g., green zone), he or she can be given feedback that he or she is in the healthy range (e.g., via colors or a text message). He or she can also be given messages to shape a positive mindset and congratulations. If the athlete is below the healthy range by a less than a threshold (e.g., the yellow zone), he or she can be given feedback that he or she is slightly below the healthy range. The athlete can also be given messages to shape a positive mindset and congratulations. If the athlete is below the healthy range by more than a small threshold (e.g., red zone), he or she can be given feedback that he or she is well below their healthy range. The athlete can also be given messages to shape a positive mindset (e.g., "you can meet this challenge."). Athletes can be encouraged to reach out to others for support, and they can receive personalized supportive information.

The use of the weight management systems described herein is not limited to treatment of congestive heart failure, eating disorders, athletes, or obesity. For example, the weight management systems described herein may be useful in the treatment of OCD, anxiety, depression, cardiovascular disease, hypertension, stroke, gallbladder disease, Type 2 diabetes, bone and joint diseases, sleep apnea, osteoarthritis, gout, fatty liver disease, kidney disease, complications in pregnancy, and some types of cancers, including endometrial cancer, breast cancer, ovarian cancer, prostate cancer, liver cancer, gallbladder cancer, kidney cancer, and colon cancer.

In any of the embodiments described herein, the measured weight can be provided to the user intermittently (i.e., less than the non-numerical feedback is provided). For example, the numerical information can be provided to the user only once every set number of times that a weight measurement is taken (e.g., only once for every five or 10 measurements). As another example, the numerical information can be provided to the user once every set period of time (e.g., once a week or once every two weeks). In some embodiments, the user can be asked for feedback as to the user's reaction to receiving the measured weight (e.g., anxious, acceptable, etc.), and the weight management system can adjust the frequency of providing the numerical feedback accordingly. The intermittent numerical weight information can supplement the non-numerical feedback received by the user.

The systems and methods described herein advantageously improve the well-being of individuals by enabling them to overcome challenges associated with receiving numerical weight measurements, including destructive obsession with weight and/or anxiety, while simultaneously achieving desired health goals.

It should be understood that any feature described herein with respect to one embodiment can be combined with or substituted for any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for weight management comprising:
    a platform;
    a weight sensor configured to measure a weight of a user when the user is positioned on the platform; and
    a controller configured to provide non-numerical feedback when the user is positioned on the platform, wherein the non-numerical feedback is provided on a display fewer times than the user is positioned on the platform, wherein the non-numerical feedback is customized based on one or more user inputs, wherein the controller is configured to have first, second, and third settings,
    wherein in the first setting, the controller is configured to obtain a weight measurement from the user positioned on the platform without providing the weight measurement to the user;
    wherein in the second setting, the controller is configured to obtain a weight measurement from the user positioned on the platform and to provide the non-numerical feedback to the user, when the user stands on the platform regardless of the weight measurement;
    wherein in the third setting, the controller is configured to obtain a weight measurement from the user positioned on the platform and to provide the non-numerical feedback to the user;
    wherein the one or more non-numerical outputs are a visual narrative that progresses through a story each time the user is positioned on the platform independent from measuring the weight; and
    wherein the progression of the visual narrative is based on previous engagement with the platform.

2. The device of claim 1, wherein the display is configured to delay providing the one or more non-numerical outputs after at least one minute delay after the weight measurement is taken.

3. The device of claim 1, wherein the visual narrative comprises one or more visual, audible, or textual elements.

4. The device of claim 1, wherein the controller is further configured to be customized by a user with one non-numerical outputs provided by a third party.

5. A method of managing weight comprising:
    measuring a patient's weight with a weight management device of claim 1;
    providing the one or more non-numerical outputs to the patient on the display of the weight management device, wherein the one or more non-numerical outputs are entirely unrelated to the measured weight so as to promote a positive mindset for the user; and
    sending the weight measurement to medical personnel without providing the weight measurement to the patient.

6. The method of claim 5, wherein the method is used to treat congestive heart failure, anorexia nervosa, athletes, eating disorders, obesity, obsessive-compulsive disorder, anxiety, depression, cardiovascular disease, hypertension, stroke, gallbladder disease, diabetes, bone or joint disease, sleep apnea, osteoarthritis, gout, fatty liver disease, kidney disease, complications in pregnancy, or cancer.

7. A method of managing weight for patients with anorexia nervosa comprising:
    measuring a patient's weight with a weight management device of claim 1;
    providing the one or more non-numerical outputs to the patient on the display of the weight management device, wherein the one or more non-numerical outputs are entirely unrelated to the measured weight so as to promote a positive mindset for the user; and
    sending the weight measurement to medical personnel without providing the weight measurement to the patient.

* * * * *